(12) United States Patent
Van Funderburk

(10) Patent No.: US 9,496,733 B2
(45) Date of Patent: Nov. 15, 2016

(54) OPTICAL COMMUNICATIONS BETWEEN AN IMPLANTABLE MEDICAL DEVICE AND EXTERNAL CHARGER

(71) Applicant: Boston Scientific Neuromodulation Corporation, Valencia, CA (US)

(72) Inventor: Jeffery Van Funderburk, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 248 days.

(21) Appl. No.: 14/470,879

(22) Filed: Aug. 27, 2014

(65) Prior Publication Data

US 2015/0077050 A1   Mar. 19, 2015

Related U.S. Application Data

(60) Provisional application No. 61/877,877, filed on Sep. 13, 2013.

(51) Int. Cl.
| | |
|---|---|
| *H02J 7/00* | (2006.01) |
| *A61N 1/378* | (2006.01) |
| *H02J 7/02* | (2016.01) |
| *A61N 1/372* | (2006.01) |
| *H02J 5/00* | (2016.01) |

(52) U.S. Cl.
CPC ........... *H02J 7/0047* (2013.01); *A61N 1/3787* (2013.01); *A61N 1/37223* (2013.01); *A61N 1/37247* (2013.01); *H02J 5/005* (2013.01); *H02J 7/025* (2013.01); *H02J 7/0004* (2013.01); *H02J 7/0042* (2013.01)

(58) Field of Classification Search
CPC ...... H02J 5/005; H02J 7/0042; H02J 7/0047; H02J 7/025; H02J 7/0004; A61N 1/3787; A61N 1/37223
USPC ......................................... 320/107, 108, 137
See application file for complete search history.

(56) References Cited

U.S. PATENT DOCUMENTS

| | | | |
|---|---|---|---|
| 4,361,153 A | 11/1982 | Slocum et al. | |
| 5,556,421 A | 9/1996 | Prutchi et al. | |

(Continued)

OTHER PUBLICATIONS

Katsuhige Inoue et al., Transcutaneous Optical Telemetry System with Infrared Laser Diode, ASAIO Journal 1998, 1998, 841-844.

*Primary Examiner* — Edward Tso
*Assistant Examiner* — Aaron Piggush
(74) *Attorney, Agent, or Firm* — Lewis, Reese & Nesmith, PLLC

(57) ABSTRACT

An improved medical device system is disclosed in which system devices communicate optically. An Implantable Medical Device (IMD) is disclosed having a hermetic window assembly on one side of its case, through which a photoemitter and photodetector can transmit and receive optical signals. The optical radiation in the signals is preferably visible, which permits communications from the IMD to be seen prior to implantation and even after implantation through a patient's tissue. External controllers for adjusting therapeutic operation of the IMD, external chargers for providing a magnetic charging field to charge a battery in the IMD, and combined external controllers/chargers are also disclosed that optically communicate with the IMD through the patient's tissue. The optical communication capabilities of the external charger are particularly useful in determining misalignment with the IMD.

20 Claims, 21 Drawing Sheets

(56) References Cited

U.S. PATENT DOCUMENTS

| | | |
|---|---|---|
| 5,730,125 A | 3/1998 | Prutchi et al. |
| 5,902,326 A | 5/1999 | Lessar et al. |
| 6,243,608 B1 | 6/2001 | Pauly et al. |
| 6,516,227 B1 | 2/2003 | Meadows et al. |
| 6,944,488 B2 | 9/2005 | Roberts |
| 6,993,384 B2 | 1/2006 | Bradley et al. |
| 7,351,921 B1 | 4/2008 | Haller et al. |
| 7,447,533 B1 | 11/2008 | Fang et al. |
| 7,684,869 B2 | 3/2010 | Bradley et al. |
| 7,813,778 B2 | 10/2010 | Benaron et al. |
| 8,012,189 B1 | 9/2011 | Webb et al. |
| 8,239,038 B2 | 8/2012 | Wolf, II |
| 8,290,592 B2 | 10/2012 | Kane et al. |
| 8,311,638 B2 | 11/2012 | Aghassian |
| 8,457,756 B2 | 6/2013 | Rahman |
| 8,473,066 B2 | 6/2013 | Aghassian et al. |
| 2007/0244524 A1 | 10/2007 | Qu et al. |
| 2008/0027293 A1 | 1/2008 | Vodermayer et al. |
| 2008/0027500 A1 | 1/2008 | Chen |
| 2009/0076353 A1 | 3/2009 | Carpenter et al. |
| 2009/0118816 A1 | 5/2009 | Kipshidze et al. |
| 2010/0022856 A1 | 1/2010 | Cinbis et al. |
| 2010/0106220 A1* | 4/2010 | Ecker ................ A61B 5/02028 607/60 |
| 2010/0137948 A1 | 6/2010 | Aghassian et al. |
| 2011/0087307 A1 | 4/2011 | Carbunaru et al. |
| 2012/0108923 A1 | 5/2012 | Cinbis et al. |
| 2012/0235636 A1* | 9/2012 | Partovi .................. H02J 7/025 320/108 |
| 2012/0259393 A1 | 10/2012 | Benabid et al. |
| 2013/0096651 A1 | 4/2013 | Ozawa et al. |
| 2013/0123881 A1 | 5/2013 | Aghassian |

\* cited by examiner

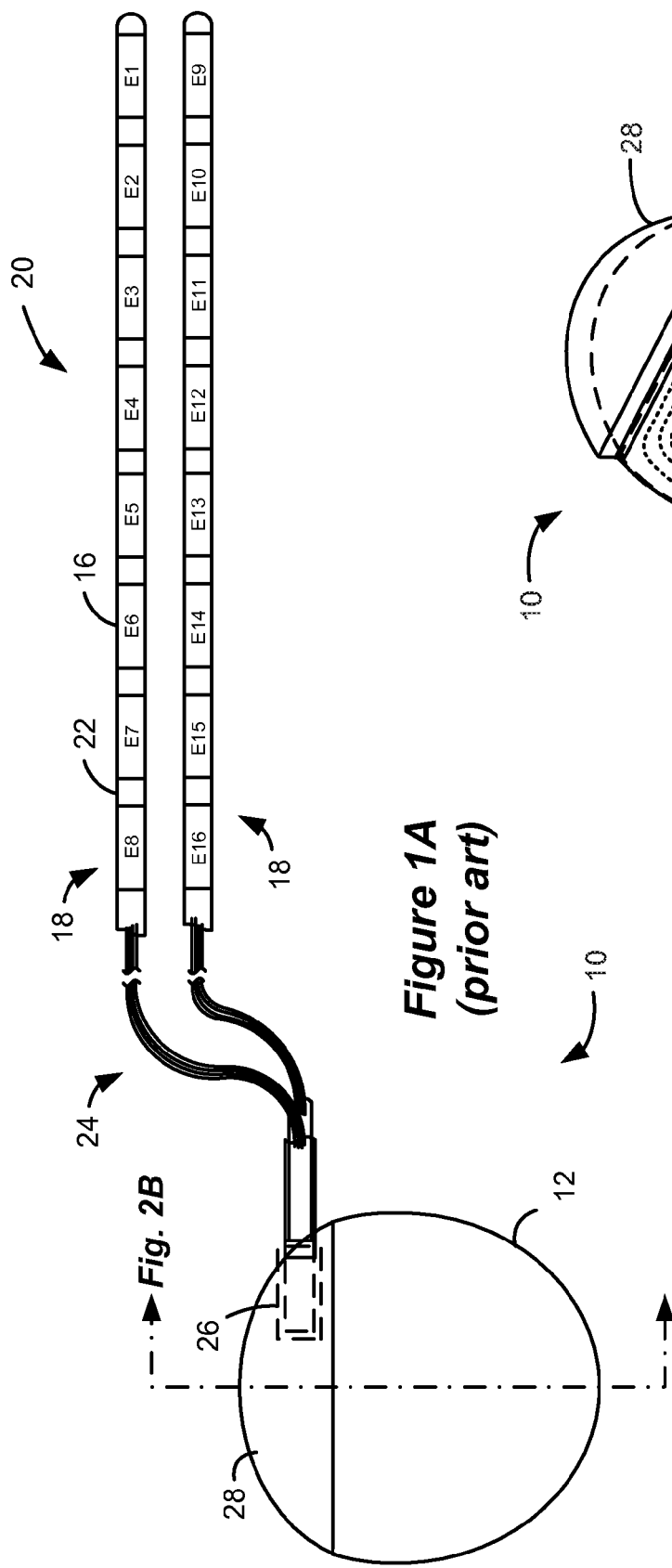
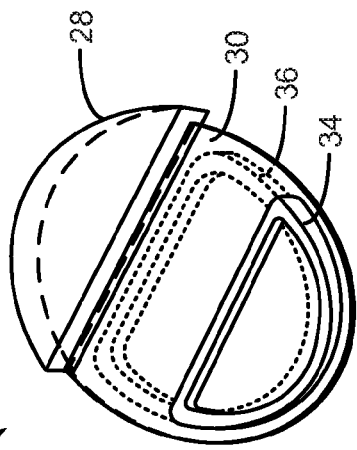
Figure 1A (prior art)
Figure 1B (prior art)

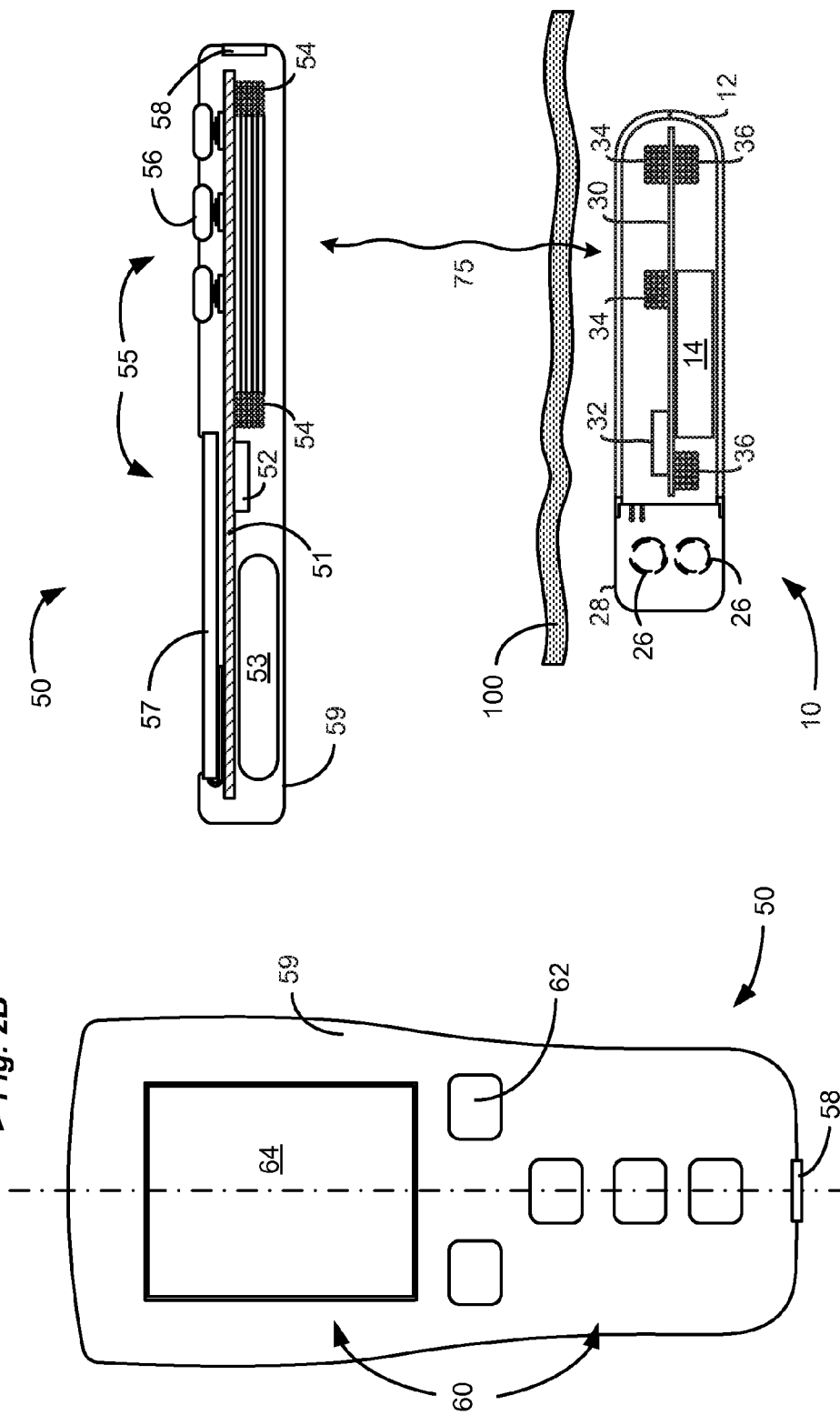

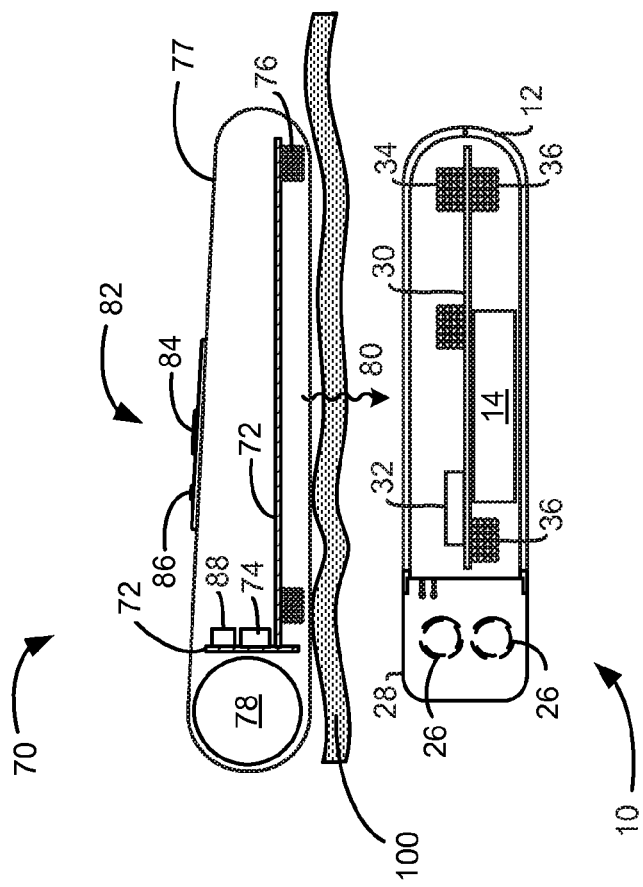
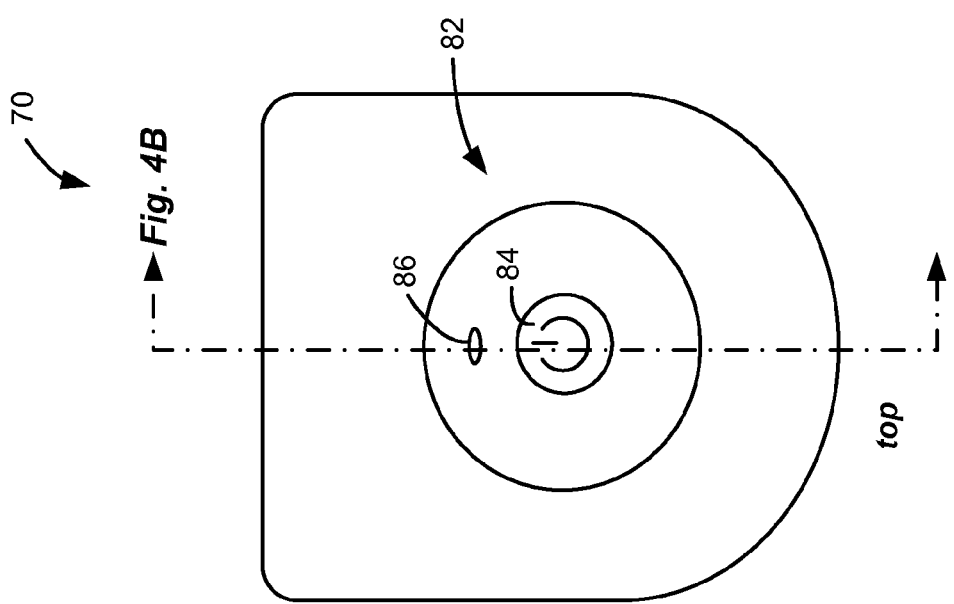
*Figure 4A (prior art)*
*Figure 4B (prior art)*

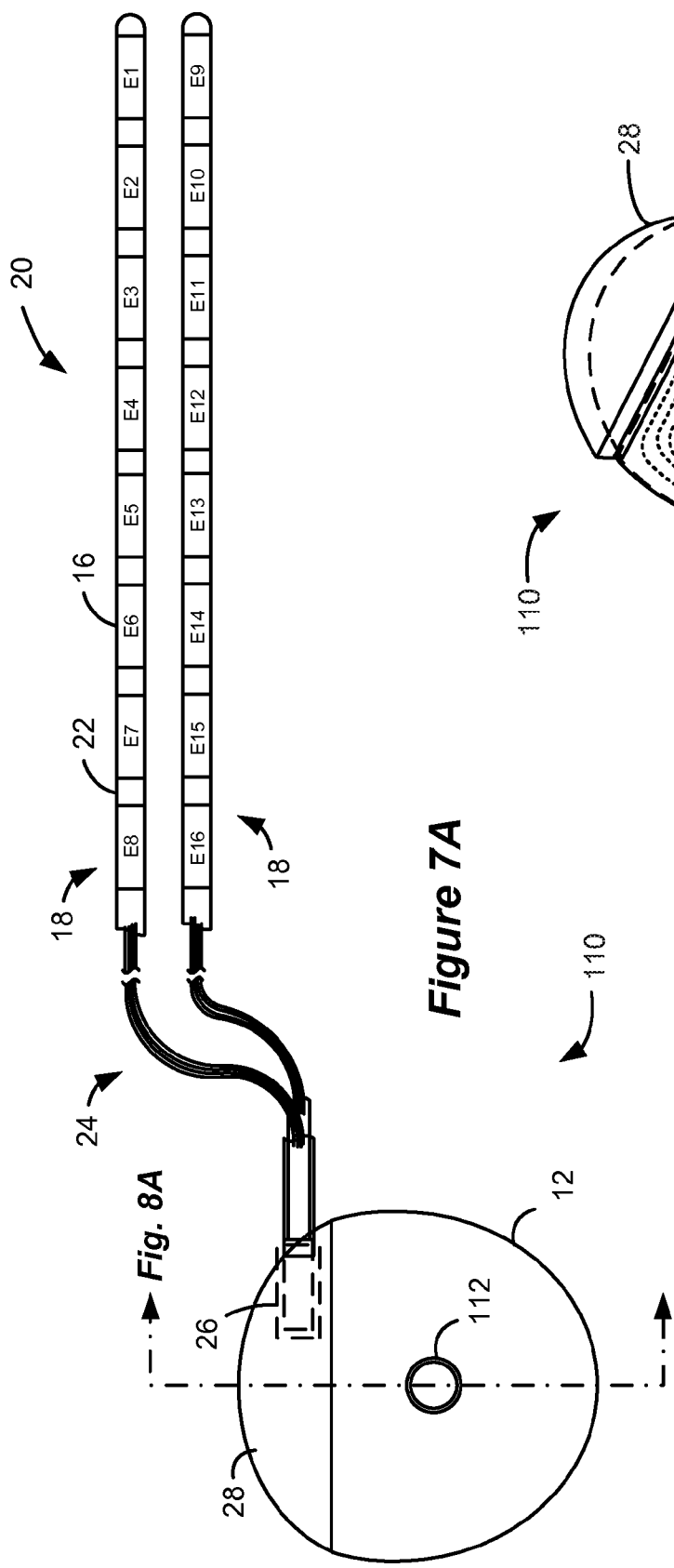
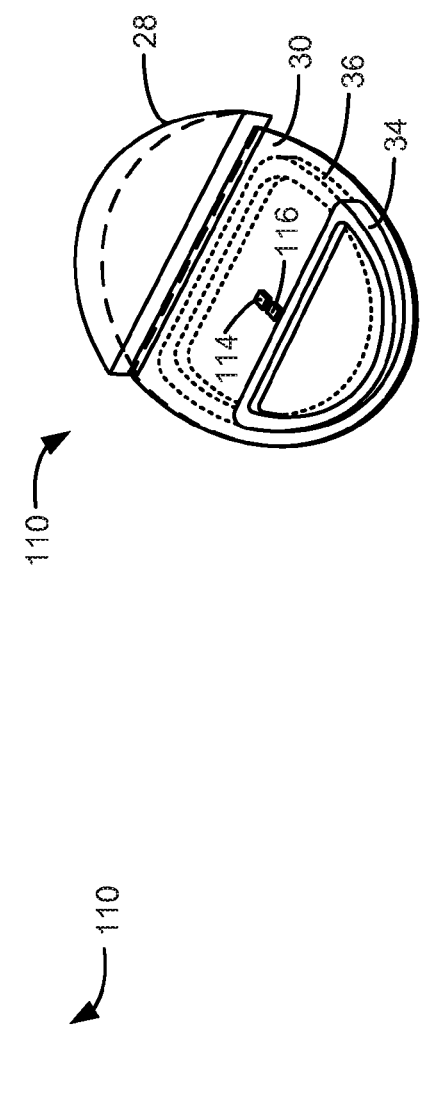
Figure 7A
Figure 7B

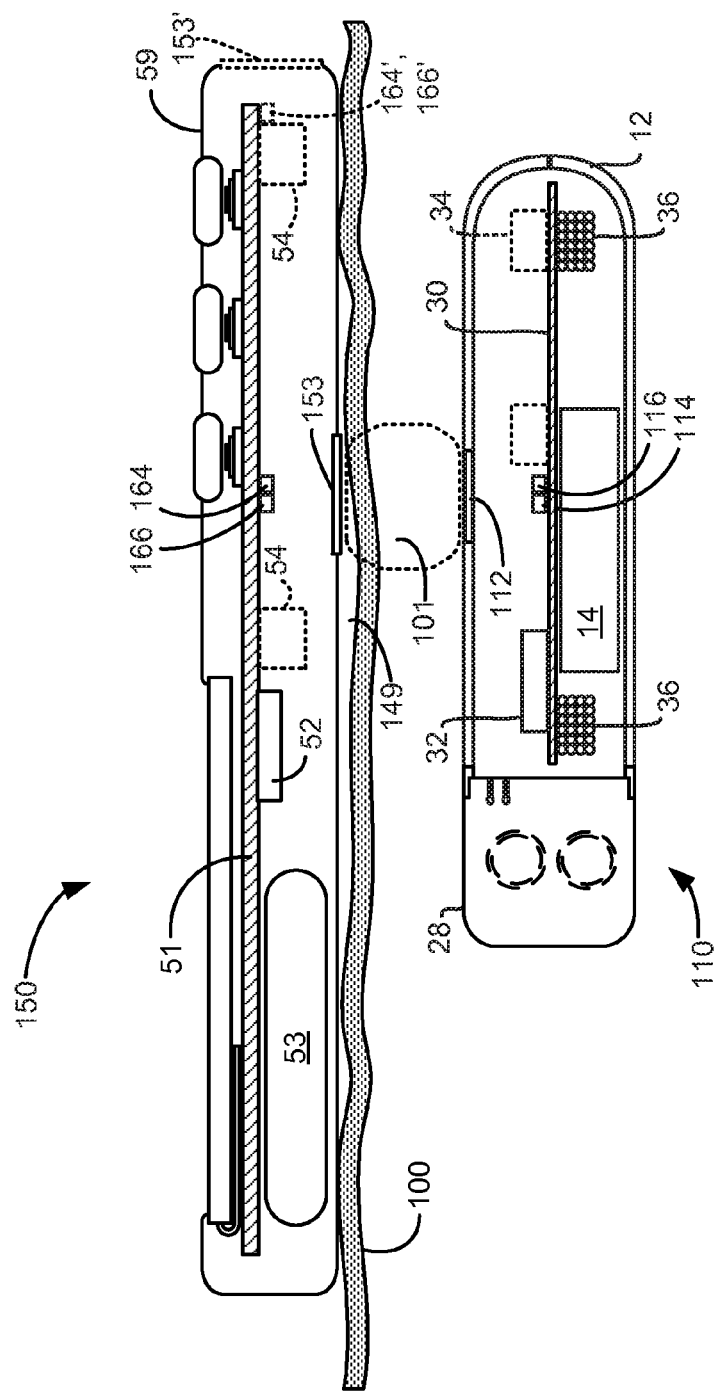
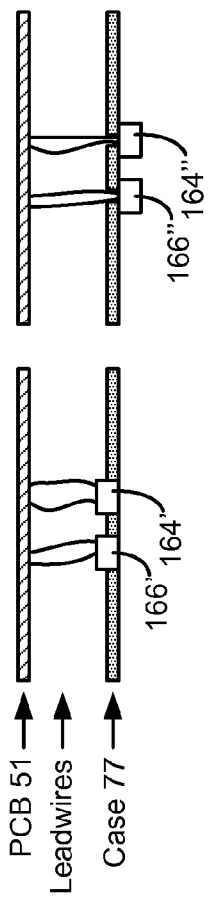
Figure 9

$(I_a > I_t)$ $(I_a < I_t)$

OPTICAL COMMUNICATIONS BETWEEN AN IMPLANTABLE MEDICAL DEVICE AND EXTERNAL CHARGER

CROSS REFERENCE TO RELATED APPLICATIONS

This is a non-provisional of U.S. Provisional Patent Application Ser. No. 61/877,877, filed Sep. 13, 2013, which is incorporated herein by reference in its entirety, and to which priority is claimed.

This application is related to U.S. Provisional Patent Application Ser. No. 61/877,871, filed Sep. 13, 2013, entitled "Window in a Case of an Implantable Medical Device to Facilitate Optical Communications With External Devices," which is incorporated herein by reference in its entirety.

FIELD OF THE INVENTION

The present invention relates to wireless communications with and wireless charging of an implantable medical device such as an implantable pulse generator.

BACKGROUND

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A and 1B, a SCS system typically includes an Implantable Pulse Generator (IPG) 10, which includes a biocompatible device case 12 formed of metallic material such as titanium for example. The case 12 typically holds the circuitry and battery 14 (FIG. 2B) necessary for the IPG to function, although IPGs can also be powered via external RF energy and without a battery. The IPG 10 is coupled to electrodes 16 via one or more electrode leads (two such leads 18 are shown), such that the electrodes 16 form an electrode array 20. The electrodes 16 are carried on a flexible body 22, which also houses the individual signal wires 24 coupled to each electrode. In the illustrated embodiment, there are eight electrodes on each lead, although the number of leads and electrodes is application specific and therefore can vary. The leads 18 couple to the IPG 10 using lead connectors 26, which are fixed in a header 28 comprising epoxy for example, which header is affixed to the case 12. In a SCS application, distal ends of electrode leads 18 are typically implanted on the right and left side of the dura within the patient's spinal cord. The proximal ends of leads 18 are then tunneled through the patient's tissue 100 to a distant location such as the buttocks where the IPG 10 is implanted, where the proximal leads ends are then connected to the lead connectors 26.

As shown in cross section in FIG. 2B, the IPG 10 typically includes an electronic substrate assembly including a printed circuit board (PCB) 30 containing various electronic components 32 necessary for operation of the IPG 10, some of which are described subsequently. Two coils are generally present in the IPG 10: a telemetry coil 34 used to transmit/receive data to/from an external controller 50 (FIG. 2A); and a charging coil 36 for charging or recharging the IPG's battery 14 using an external charger 70 (FIG. 4A). These coils 34 and 36 are also shown in the perspective view of the IPG 10 in FIG. 1B, which omits the case 12 for easier viewing. Although shown as inside in the case 12 in the Figures, the telemetry coil 34 can alternatively be fixed in header 28. Coils 34 and 36 may alternative be combined into a single telemetry/charging coil.

FIG. 2A shows plan views of the external controller 50, and FIG. 2B shows it in cross section and in relation to the IPG 10 during a communication session. The external controller 50, such as a hand-held portable programmer or a clinician's programmer, is used to set or adjust the therapy settings the IPG 10 will provide to the patient (such as which electrodes 16 are active, whether such electrodes sink and source current, and the duration, frequency, and amplitude of pulses formed at the electrodes, etc.). The external controller 50 can also act as a receiver of data from the IPG 10, such as various data reporting on the IPG's status, the level of the IPG 10's battery 14, and other parameters measured or logged at the IPG 10. Such communications can occur bi-directionally via link 75.

As shown in FIG. 2B, the external controller 50 contains a PCB 51 on which electronic components 52 are placed to control operation of the external controller 50. The external controller 50 is powered by a battery 53, but could also be powered by plugging it into a wall outlet for example. A telemetry coil 54 is also present in the external controller 50, which will be discussed further below. A case 59, typically made of plastic, houses the internal components of the external controller 50. The external controller 50 typically comprises a user interface 55 similar to that used for a portable computer, cell phone, or other hand held electronic device, including touchable buttons 56 and a display 57. A port 58 allows the external controller to be electrically coupled to a power source, to other computer devices, etc.

Wireless data transfer between the external controller 50 and the IPG 10 via link 75 takes place via magnetic inductive coupling between coils 54 and 34, either of which can act as the transmitter or the receiver to enable two-way communication between the two devices. Referring to FIG. 3, which depicts circuitry in these devices, when a series of digital data bits (FSK data 47) is to be sent from the external controller 50 to the IPG 10, control circuitry 60 (e.g., a microcontroller) provides these bits in sequence to a modulator 61. Modulator 61 energizes coil 54 with an alternating current (AC) whose frequency is modulated in accordance with the state of the data bit currently being transferred in accordance with a Frequency Shift Keying (FSK) protocol. For example, the coil 54 may nominally be tuned to resonate at 125 kHz in accordance with the inductance of the coil 54 and a tuning capacitor (not shown), which data states '0' and '1' altering this center frequency to $f_0$=121 kHz and $f_1$=129 kHz respectively. The frequency-modulated current through the coil 54 in turn generates a frequency-modulated magnetic field comprising link 75, which in turn induces a frequency-modulated current in the IPG's telemetry coil 34. This received signal is demodulated 43 back into the series of digital data bits, and sent to control circuitry 38 (e.g., a microcontroller) in the IPG 10 for interpretation. Data telemetry in the opposite direction from IPG 10 to external controller 50 occurs similarly via modulator 41 and demodulator 62. Inductive coupling via link 75 occurs transcutaneously, i.e., through the patient's tissue 100.

Other means for electro-magnetically communicating between the external controller 50 and IPG 10 via link 75 are known as well, including RF communications such as Bluetooth, Zigbee, etc., that are enabled patch, wire, or slot antennas. In this instance, link 75 would comprise a longer-range electromagnetic field, rather than the near-field magnetic field enabled by coils 54 and 34.

FIG. 4A shows a plan view of the external charger 70, and FIG. 4B shows it in cross section and in relation to the IPG 10 during a charging session. The external charger 70 is used to wirelessly charge (or recharge) the IPG's battery 14, and includes at least one PCB 72 (two are shown; see U.S. Patent Application Publication 2008/0027500); electronic components 74, some of which are subsequently discussed; a charging coil 76; and a battery 78 for providing operational power for the external charger 70 and for the production of a magnetic charging field 80 from the coil 76. These components are typically housed within a case 77, which may be made of plastic for example.

The external charger 70 has a user interface 82, which typically comprises an on/off switch 84 to activate the production of the magnetic charging field 80; an LED 86 to indicate the status of the on/off switch 84; and a speaker 88. The speaker 88 emits a "beep" for example if the external charger 70 detects that its charging coil 76 is not in good alignment with the charging coil 36 in the IPG 10 during a charging session, as discussed further below. The external charger 70 is sized to be hand held and portable, and may be placed in a pouch around a patient's waist to position the external charger 70 in alignment with the IPG 10 during a charging session. Typically, the external charger 70 is touching the patient's tissue 100 during a charging session as shown, although the patient's clothing or the material of the pouch may intervene.

Wireless power transfer from the external charger 70 to the IPG 10 occurs by magnetic inductive coupling between coils 76 and 36. Referring to FIG. 5, when the external charger 70 is activated (e.g., on/off switch 84 is pressed), a charging circuit 94 under control of control circuitry 92 (e.g., a microcontroller) energizes coil 76 with a non-data-modulated AC current (Icharge) to create the magnetic charging field 80. The frequency of the magnetic charging field may be on the order of 80 kHz for example, and may be set by the inductance of the coil 76 and the capacitance of a tuning capacitor (not shown). The magnetic charging field 80 induces a current in the IPG 10's charging coil 36, which current is rectified 44 to DC levels and used to provide a charging current (Ibat) to recharge the IPG's battery 14, perhaps under the control of charging and battery protection circuitry 46 as shown. This again occurs transcutaneously.

The IPG 10 can also communicate data back to the external charger 70 using Load Shift Keying (LSK) telemetry. Relevant data, such as the capacity of the battery, is sent from control circuitry 38 in the IPG 10 to a LSK modulator 40, which creates a series of digital data bits (LSK data 48). This data is input to the gate of a load transistor 42 to modulate the impedance of the charging coil 36 in the IPG 10. Such modulation of the charging coil 36 is detectable at the external charger 70 due to the mutual inductance between the coils 76 and 36, and will change the magnitude of the AC voltage needed at coil 76 (Vcoil) to drive the charging current, Icharge. If coil 36 is shorted (LSK data=1), Vcoil increases ($Vcoil_1$) to maintain Icharge; if not shorted (LSK data=0), Vcoil decreases ($Vcoil_0$), as shown in the waveform in FIG. 5. LSK demodulator 96 in the external charger 70 can detect these changes in Vcoil ($\Delta V$) to recover the series of digital data bits, which data is then received at control circuitry 92 so that appropriate action can be taken, such as ceasing production of the magnetic charging field 80 (i.e., setting Icharge to zero) because the battery 14 in the IPG 10 is full. Note that the nature of LSK telemetry as described here only allows for telemetry from the IPG 10 to the external charger 70 when a magnetic charging field 80 is being produced. See, e.g., U.S. Patent Application Publication 2013/0123881 for further details regarding the use of LSK telemetry in an external charger system.

The inventor is concerned about certain problems with traditional means of wireless communications between an external controller 50 and the IPG 10, and with traditional means of charging an IPG 10 using an external charger 70. The inventor's concerns regarding communications are discussed first.

As is known, wireless communications to and from the IPG 10 can be attenuated by the conductive material of the case 12 as well as other conductive structures present in the IPG 10 and the external controller 50. Especially when magnetic induction is used as the means for establishing communication link 75 for example, the generated AC magnetic fields will create eddy currents in such conductive structures, which essentially act as an unwanted sink for the energy in the field, thus reducing the distance at which communications and charging can reliably occur. See, e.g., U.S. Pat. No. 8,457,756.

Previous IPGs 10 have used non-conductive ceramic materials for the case 12, see, e.g., U.S. Pat. No. 7,351,921, which would reduce attenuation of wireless communications in IPGs using internal coils. However, ceramic materials are also brittle and difficult to work with. Ceramic case components further require brazing to mechanically couple them together or to other metallic components, which can be difficult to perform.

Previous approaches have used optical radiation instead of electromagnetic fields as the means to communicate with an implantable medical device. For example, U.S. Pat. No. 5,556,421 discloses a pacemaker which has photoemitter such as a Light Emitting Diode (LED), and a photodetector such as a phototransistor, for respectively transmitting data to and receiving data from a device external to the patient. See FIG. 15 of the '421 patent. However, in the '421 patent, the photoemitter and photodetector are contained within the header of the pacemaker, similar to the header 28 for the IPG 10 described earlier (FIG. 1A). The header is described in the '421 patent as suitably translucent to the wavelengths of optical radiation at which the LED and photodiode operate (within the range of 640 to 940 nm).

The inventor however finds the optical communication approach of the '421 patent to be problematic, in particular because the optical elements are contained within the header of the implantable medical device. The three-dimensional shape of the header makes optical transmission and reception difficult, as optical radiation will reflect at the outer surfaces of the header and other reflective components in the header, such as the lead connectors 26 (see, e.g., FIG. 1A). Optical radiation will also refract, attenuate, and disperse in the header material. Additionally, there may be little room in the header to accommodate optical elements. This is particularly problematic in a SCS IPG, which comprises many electrodes (e.g., 16 or 32), and hence requires long lead connectors 26, or more lead connectors, in the header 28. Providing optical elements in the header provides further concerns that additional feedthrough pins between the header and the interior of the case would be necessary, complicating IPG design and potentially impacting reliability.

U.S. Pat. No. 6,243,608 also discloses a pacemaker that can communicate optically with an external device, although once again in this reference, the optical element is contained in the header, thus suffering from the same problems discussed above with reference to the '421 patent. (Specifically, this pacemaker has only a photoemitter and thus can only communicate optically with the external device in one direction; communication from the external device to the pacemaker occurs via magnetic induction between two coils). In the text associated with one embodiment, see FIG. 6 of the '608 patent, it is mentioned that the photoemitter can be located in an electronics module inside the pacemaker case. But in this instance, the photoemitter transmits light from inside the case to the translucent header. This too is not practical. Although not discussed in detail in the '608 patent, this approach requires porting the optical radiation through the feedthrough between the case and header in some fashion, which would attenuate the radiation, and complicate feedthrough design. It is noted that a mirror may need to be provided in the header to direct the optical radiation to the external device, or that a portion of the outer surface of the header be shaped as a lens, both of which are complicated, expensive, and could be expected to attenuate the radiation.

U.S. Pat. No. 7,447,533 discloses a pacemaker in which a photoemitter and photodetector are used to detect a physiological parameter, such as blood flow (photoplethysmography). In one example, see FIGS. 7 and 8 of the '533 patent, an aperture is formed in one of the flat sides of the case that accommodates an assembly containing the optical elements. Once positioned in place, the assembly is welded to the case. Nonetheless, the '533 patent is not relevant to the inventor's concern regarding communications between an implant and an external device. The optical elements in the '533 are not used to send and receive a series of data bits, and are not used to communicate optical radiation externally to the implant. Instead, the photoemitter provides radiation that reflects off the patient's tissue, which reflection is detected at the implant's photodetector to determine the physiological parameter. (If a dual-wavelength photoemitter is used, the wavelengths are enabled in an alternating fashion). For communications between the implant and the external device, the '533 patent instead uses an electromagnetic antenna operable with radio waves (e.g., 10-15 MHz). U.S. Pat. No. 5,902,326 is similar, although in this patent the optical elements are used to detect a different physiological parameter, namely blood oxygen content (oximetry).

U.S. Patent Application Publication 2009/0076353 also comprises a pacemaker having an aperture on one of the flat sides of the case that accommodates an optical sensor assembly, which again can be welded to the case. However, the unique particulars of the '353 Publication render it unsuitable for data communication external to the implant. The optical sensor assembly is designed to detect yet another physiological parameter, in this case analytes such as Potassium ions. As described in the '353 Publication, such analytes are designed to diffuse through the optical sensor assembly where they meet with a chemical sensing element. Photoemitters in the assembly are made to reflect off of this chemical sensing element. The chemical sensing element's optical properties change in the presence of the analyte, and so reflections are received at a photodetector in the optical sensor assembly to measure the analyte. Indeed, the unique particulars of this publication render it unsuitable for external data communications, as an overlying cover layer is included to block ambient light from entering the optical sensor assembly, and also to prevent the light from the photoemitters from escaping the optical sensor assembly.

The inventor is also concerned about shortcomings concerning charging an implantable medical device battery. In particular, the inventor is concerned that charging is hampered by difficulty in determining the alignment between the external charger 70 and the IPG 10.

It is generally desirable to charge the IPG's battery 14 as quickly as possible to minimize inconvenience to the patient. One way to decrease charging time is to increase the strength of the magnetic charging field 80 by increasing Icharge in the charging coil 76 of the external charger 70. Increasing the magnetic charging field 80 will increase the current/voltage induced in the coil 36 of the IPG 10, which increases the battery charging current, Ibat, hence charging the battery 14 faster.

However, the strength of the magnetic charging field 80 can only be increased so far before heating becomes a concern. Heating is an inevitable side effect of inductive charging using magnetic fields, and can result because of activation of relevant charging circuitry in the external charger 70 or IPG 10, or as a result of eddy currents formed by the magnetic charging field 80 in conductive structures in either device. Heating is a safety concern. The external charger 70 is usually in contact with the patient's tissue 100 during a charging session, and of course the IPG 10 is inside the patient. If the temperature of either exceeds a given safe temperature, the patient's tissue may be aggravated or damaged.

The alignment between the external charger 70 and the IPG 10 can affect heating, as shown in FIGS. 6A and 6B. In FIG. 6A, the charging coils 76 and 36 in the external charger 70 and the IPG 10 are well aligned, because the axes 76' and 36' around which the coils 76 and 36 are wound are collinear. As such, these coils 76 and 36 are well coupled electrically, meaning that a higher percentage of the power expended at coil 76 in creating the magnetic charging field 80 is actually received at coil 36, which leads to higher values for Ibat. In FIG. 6B, the charging coils 76 and 36 are laterally misaligned (d), which reduces the electrical coupling between the coils. Increasing the vertical distance x between the coils 76 and 36 (FIG. 6C), or increasing the angle (θ) between the preferably parallel planes in which they reside (FIG. 6D), will also reduce coupling.

If it is desired that the alignment scenarios of FIGS. 6A and 6B charge the battery 14 at the same rate (Ibat=Y), then a higher value for Icharge (Icharge>X) will be needed in the misaligned scenario of FIG. 6B compared to the well-aligned scenario of FIG. 6A (Icharge=X). A higher value for Icharge in FIG. 6B will create a more intense magnetic charging field 80 that tend to increase the temperature of the environment (T>Z) when compared to the temperature of the environment in FIG. 6A (T=Z). If it is desired that the temperature be the same for both scenarios, then Icharge can be lowered in FIG. 6B, but this will also lower Ibat, and hence the battery 14 in that scenario would take longer to charge. In short, misalignment between the external charger 70 and the IPG 10 is not desired.

Accordingly, the art has disclosed several manners for determining misalignment between an external charger and an IPG, which techniques usually result in some form of user-discernible output letting the patient know when alignment is poor (such as via speaker 88 discussed earlier). Such techniques may also inform a patient how to fix the alignment, such as by indicating a direction the external charger should be moved relative to the IPG 10. See, e.g., U.S. Pat. Nos. 8,473,066 and 8,311,638.

Previous external charger alignment techniques however are difficult to implement, and may not precisely determine alignment as they rely on inferences gleaned from electrical measurements taken during the charging session. For example, one prior art alignment techniques relies on determining the loading of the charging coil in the external charger during production of the magnetic charging field. Specifically, the voltage across the charging coil (Vcoil) is reviewed at the external charger and compared to a Vcoil threshold to determine alignment. This technique though suffers in its inability to distinguish between the scenarios of FIGS. 6B and 6C for example. In either of these scenarios, Vcoil would be higher due to poor coupling, but in FIG. 6B the poor coupling arises from misalignment, whereas in FIG. 6C the alignment is as good as it can be given the IPG 10's depth (x). A modification to this technique helpful in distinguishing these scenarios requires transmitting the magnetic charging field at different frequencies and measuring the input current to the charging coil in the external charger to estimate an implant depth (x), and thus to set an appropriate Vcoil threshold. See, e.g., U.S. Patent Application Publication 2010/0137948. However, the additional overhead of having to produce magnetic charging fields at different frequencies makes this technique complicated.

Other alignment techniques require the external charger to have positioning coils in addition to the main charging coil (e.g., 76). In these techniques, measurements taken from the positioning coils during the charging session are used to determine misalignment, and to indicate a direction the external charger can be moved to improve alignment (coupling). See, e.g., U.S. Pat. Nos. 8,473,066 and 8,311,638. The requirement of additional coils beyond the main charging coil though complicates the design of the external charger.

Still other alignment techniques employ electromagnetic (EM) telemetry from the IPG, see, e.g., U.S. Patent Application Publications 2013/0096651 and 2011/0087307, which adds complexity to both the IPG and the external charger. Moreover, EM telemetry may be difficult to employ while the external charger is generating a magnetic charging field (e.g., 80), because such field is relatively strong, and may add significant noise to the EM telemetry signal. Thus it may be necessary to periodically cease the production of the magnetic charging field during a charging session to allow such telemetry from the IPG to the external charger to occur, which inconveniently lengthens the duration of the charging session.

The inventor is further concerned that LSK telemetry is limited in its ability to communicate information from the IPG the external charger. First, as noted earlier, LSK telemetry is only useful when the external charger is producing a magnetic charging field, thus hampering the ability of the IPG to communicate with the external charger, prior to starting a charging session for example. Moreover, LSK telemetry may be difficult to demodulate (e.g., FIGS. 5, 96). Vcoil, the parameter assessed by LSK demodulator 100, can vary in magnitude as the alignment between the external charger and IPG varies during a charging session, which is typical. Likewise, ΔV, the difference in Vcoil for each of the logic states being transmitted by the IPG, can vary and may also be relatively small and hard to detect depending on the coupling.

BRIEF DESCRIPTION OF THE DRAWINGS

FIGS. 1A and 1B show an Implantable Pulse Generator (IPG) and the manner in which electrodes are affixed in accordance with the prior art.

FIGS. 2A and 2B show an external controller for an IPG and the manner in which they communicate in accordance with the prior art.

FIGS. 4A and 4B show an external charger for an IPG and the manner in which they communicate in accordance with the prior art.

FIGS. 7A and 7B show an improved IPG having a window assembly for optical communications.

FIG. 9 shows an improved external controller for optically communicating with the improved IPG.

DETAILED DESCRIPTION

The inventor discloses an improved medical device system in which system devices communicate optically. An Implantable Medical Device (IMD) such as an IPG is disclosed having a hermetic window assembly on one side of its case, through which a photoemitter and photodetector can directly transmit and receive optical signals to and from the outside of the patient. The optical radiation in the optical signals is preferably visible, which permits communications from the IMD to be seen prior to implantation and even after implantation through a patient's tissue. External controllers for adjusting therapeutic operation of the IMD, external chargers for providing a magnetic charging field to charge a battery in the IMD, and combined external controllers/chargers are also disclosed that optically bi-directionally communicate with the IMD through the patient's tissue, all of which may include distal communication heads which perform optical communications with the IMD, and which may also include a charging coil. The optical communication capabilities of the external charger are particularly useful in determining and indicating misalignment with the IMD, and optical communications can occur between the external charger and the IMD regardless whether the external charger is producing a magnetic charging field or not, and without the need to cease production of the magnetic charging field. Such optical communications can also displace legacy Load Shift Keying means of communicating with the external charger, which can be difficult to demodulate.

Figure 17:
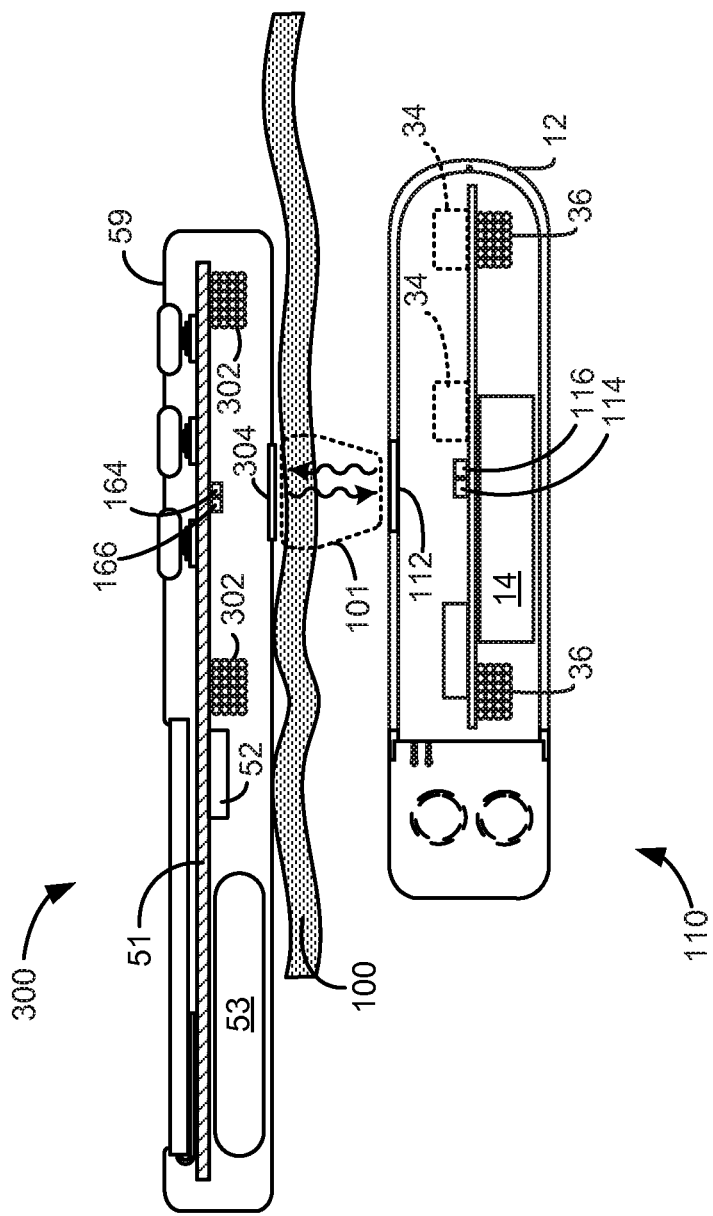
FIG. 17 shows an improved combined external controller/charger for optically communicating with the improved IPG.
Figure 18:
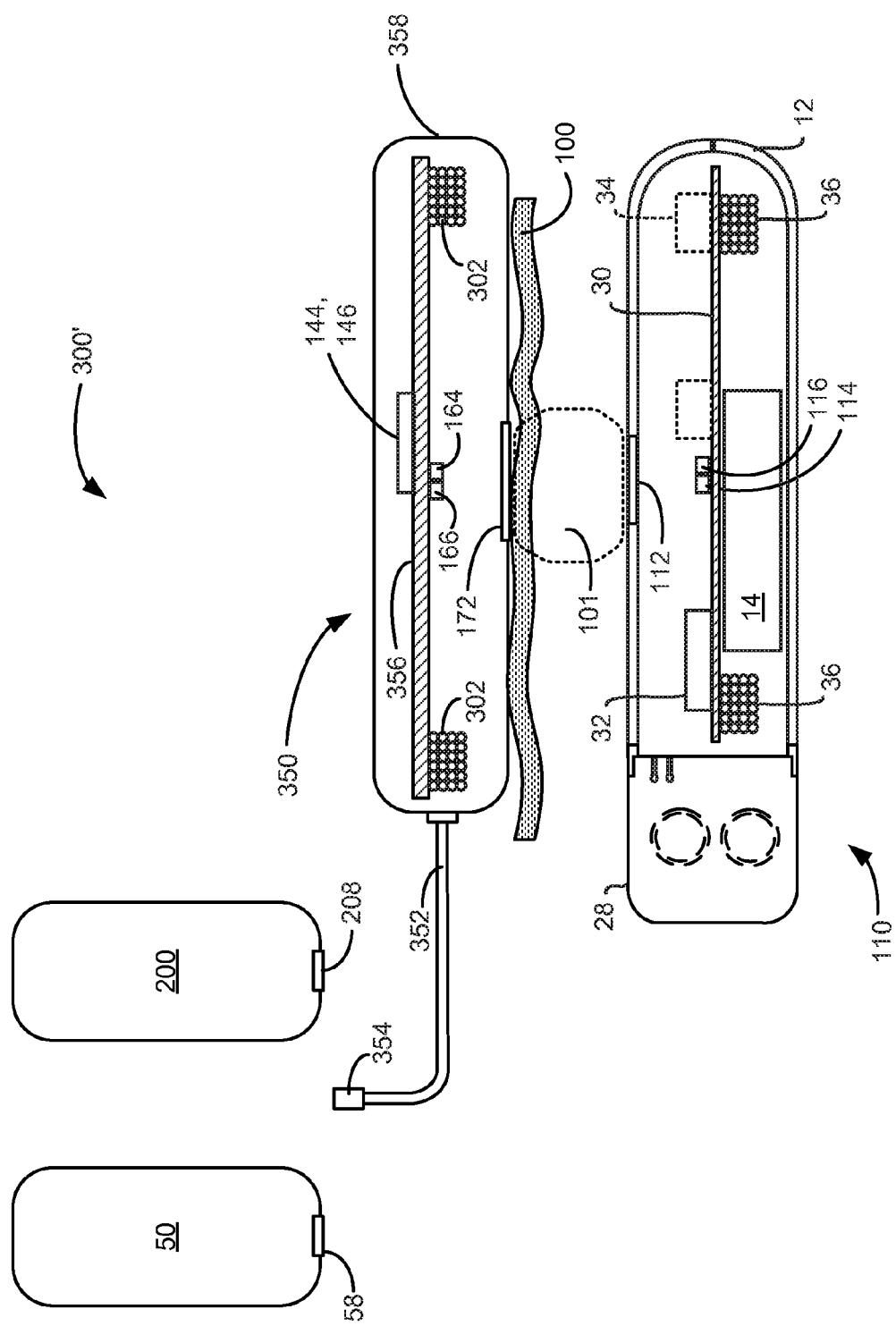
FIG. 18 shows a modified improved combined external controller/charger having a combined communication/charging head.

An improved IPG having optical communication capabilities is discussed first (FIGS. 7A-8B). External devices that can optically communicate with the improved IPG 110 are then discussed, such as an improved external controller (FIGS. 9-11), and an improved external charger (FIGS. 12-16). An integrated external device combining both communication and charging capabilities that can optically communicate with the improved IPG is discussed last (FIGS. 17-18).

FIG. 7A shows an improved IPG 110 having an optical window assembly 112 on a top flat side of its case 12 that will face outwardly of the patient when implanted. Underlying and generally centered with the window assembly 112 are optical devices, namely a photoemitter 114 and a photodetector 116, as seen in FIG. 7B (with the case 12 removed). As shown in the cross section of FIG. 8A, the photoemitter 114 and a photodetector 116 are electrically coupled to the PCB 30 of the IPG 110. Photodetector 116 may be a photo-sensitive transistor in one example, and photoemitter 114 may comprise a Light Emitting Diode (LED) or a laser diode, although other types of optical devices may also be used. As will be explained further below, having both a photoemitter 114 and photodetector 116 enables the IPG 110 to optically communicate in two directions (101a and 101b). However, this is not strictly necessary, and in uni-directional applications, only one of these devices 114 and 116 may be needed.

Figure 8A:
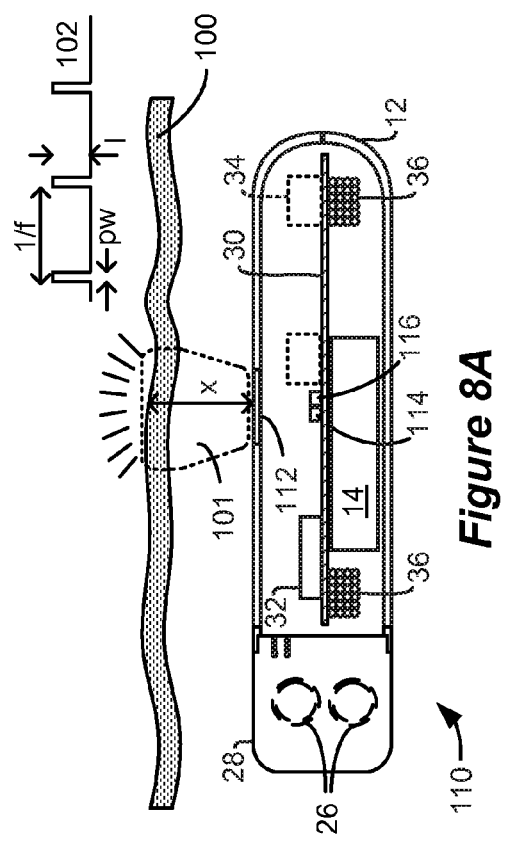
FIGS. 8A and 8B show the improved IPG in cross section.
Figure 8B:
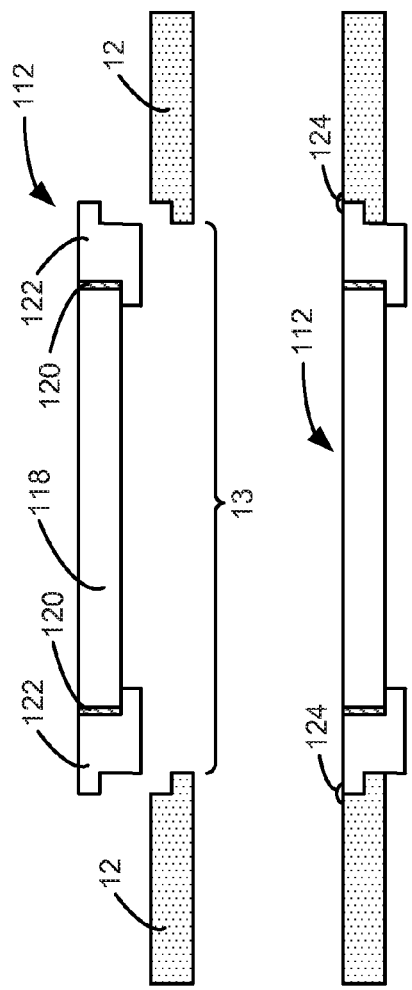

FIG. 8B shows further details of the construction of the window assembly 112, and the manner in which it is affixed to the case 12. The window assembly 112 comprises a biocompatible material and may be comprised of a glassy material, such as Schott BK10, Corning 7056, sapphire, fused silica, or quartz for example. The window 118 is made to fit in a ring-shaped collar 122 comprising titanium for example, or any other biocompatible material affixable to the material of the case 12. A filler material 120, such as gold or glass, fills the seal between the window 118 and the collar 122, and brazing is performed to melt the filler 120 and create a hermetic seal between the window 118 and the collar 122. Other brazing filler materials 120 could be used as well. As shown, the collar 122 may include a step to keep the window 118 and filler material 120 in place during the brazing process.

The side of IPG 110's case 12 is formed with a hole 13 to accommodate the window assembly 112 once its manufacture is completed. In this example, the case 12 and collar 122 include steps to allow the window assembly 112 to be placed within the hole 13 without falling through. Once positioned in place, the window assembly 112 can be welded 124 to the case 12 to create a hermetic seal. As depicted, the window assembly 112 is substantially flush with the outside surface of the case (e.g., less than 10 mils difference), which is preferred to prevent aggravation of tissue that the window assembly 112 will contact.

This design for window assembly 112, and the manner in which it is affixed to the case 12, are merely examples. Other designs and methods for providing a window 118 in an implantable medical device case 12 with good hermeticity can be used.

The photoemitter 114 and a photodetector 116 are positioned to receive and transmit optical radiation through the window 118 in the window assembly 112. In preferred embodiments, the photoemitter 114 and a photodetector 116 operate at visible wavelengths (e.g., from approximately 380 to 740 nm). This is particularly preferred when a patient, clinician, or manufacturer desires to see optical radiation emitted from the IPG 110, which is useful in several circumstances explained below. However, in other examples, the photoemitter 114 and a photodetector 116 can operate at non-visible wavelengths, such as near-Ultraviolet (e.g., 10 nm-400 nm) and near-Infrared wavelengths (e.g., 700 to 2500 nm). Essentially, any wavelength of optical radiation can be used in the context of IPG 110, so long as it (1) is not significantly attenuated by the window 118 and the patient's tissue 100, and (2) does not risk damaging the patient's tissue 100.

Because the photoemitter 114 and a photodetector 116 are hermetically sealed inside the case 12 with other IPG electronics, special care does not need to be taken to ensure that such devices are biocompatible, and thus typical, inexpensive, off-the-shelf optical components can be used for each. Photoemitter 114 and photodetector 116 may comprise a number of emitters or detectors, which may be integrated into a single optical device, although they are illustrated here separately here for clarity. Photoemitter 114 may additionally emit optical radiation at different wavelengths (e.g., different colors), while photodetector 116 may likewise be sensitive to such wavelengths.

Note that the inclusion of photoemitter 114 in the IPG 110 provides several benefits. During manufacturing or even during implantation when the IPG 110 is not yet covered by a patient's tissue 100, the photoemitter 114 (particularly if it operates at visible wavelengths) provides an easy means of verifying IPG 110 operation. For example, a manufacturer of IPG 110 can test the device and receive optical feedback concerning IPG operation by viewing the illumination of photoemitter 114 through the window assembly 112. Visual feedback can come from the photoemitter 114 in any number of forms. For example, a green light may indicate proper IPG 110 operation, and a red light may indicate faulty operation, etc. Various operational conditions can also be visually indicated. For example, a solid light may indicate one condition, a slow blinking pulse a second condition, a fast blinking pulse a third condition, etc. Combinations of blinking pulses can visually indicate various operational codes, including failure codes. For example, repeating a single pulse might indicate a first code; repeating two pulses might indicate a second code, etc. Combinations of these types of visual feedback can also be used to indicate operation, conditions, or codes. Such visual feedback can be issued by the IPG 110 of its own accord, or in response to a communication sent from the external controller 150 (FIG. 9), the external charger 170 (FIG. 12), or other external device.

A clinician can also benefit from such visual feedback provided by IPG 110. For example, when the clinician attaches the leads 18 (FIG. 1A) to the lead connectors 26 during surgery, it is important to verify that good electrical contact is established, and that there are no open or short circuits at any of the electrode contacts 16. This can be visually indicated to the clinician via photoemitter 114 before surgery is complete, in any of the foregoing manners.

A patient may also benefit from visual feedback even after the IPG 110 has been implanted in her tissue 100. In this regard, and referring to FIG. 8A, photoemitter 114 will illuminate a portion 101 of the patient's tissue 100 after implantation. The optical radiation will scatter and attenuate in the illuminated tissue 101, particularly if the IPG 110 is implanted deeper in the patient (x). Still, many implantable medical devices, including SCS IPGs 110, are purposely implanted reasonably close to the patient's skin to make implanting and explanting easier, which would reduce optical attenuation. If optical attenuation is significant enough that optical radiation from the photoemitter 114 cannot been seen at the surface of the patient's skin, the power of the photoemitter 114 can be increased. Alternatively, a patient may be instructed to view the illuminated tissue 101 in a darker environment to review relevant IPG operations, conditions, or codes.

If necessary, the window 118 in the window assembly 112 can be formed as a lens, instead of flat, to better focus the optical radiation, and to reduce the volume of the illuminated tissue 101 in which the optical radiation disperses. For example, use of a convex lens 118 would tend to focus optical radiation in the illuminated 101 tissue if radiation emitted from the photoemitter 114 is not well collimated. A convex lens 118 would also focus optical radiation dispersed in the illuminated tissue 101 toward the photodetector 116 when receiving radiation in the other direction, as subsequently explained. Traditional bulk lenses or Fresnel lenses could be used for window 118.

It should also be noted that window 118 need not be significantly optically translucent, or "see through," as glass would generally be to visible light for example. Instead, window 118 could be made of otherwise generally opaque materials that are still able to pass significant amounts of optical radiation in and out of the IPG 110. For example, window 118 could comprise a ceramic material, which could pass suitable amounts of optical radiation if made thin enough, and/or if the power and sensitivity of the photoemitter 114 and photodetector 116 are suitably high. In short, window 118 may be comprised of any material able to pass suitable amounts of optical radiation to enable the various means of optical communications disclosed, and "window" should not be construed to cover simply translucent materials.

Through-the-skin visual indications can occur in any of the ways discussed above, and can provide different sorts of information to the patient. For example, a patient could be provided with a card describing various indications important to IPG 110 operation. For example, a first indication might denote a first type of fault in the IPG 110; a second indication a second type of fault, etc. A flashing red light might indicate potentially unsafe stimulation setting, while a solid red light indicates a severe failure that caused the IPG 110 to shut down. Red indications may denote that the patient needs to contact the clinician, while green indications indicate normal IPG operation while still providing particular information.

Figure 3:
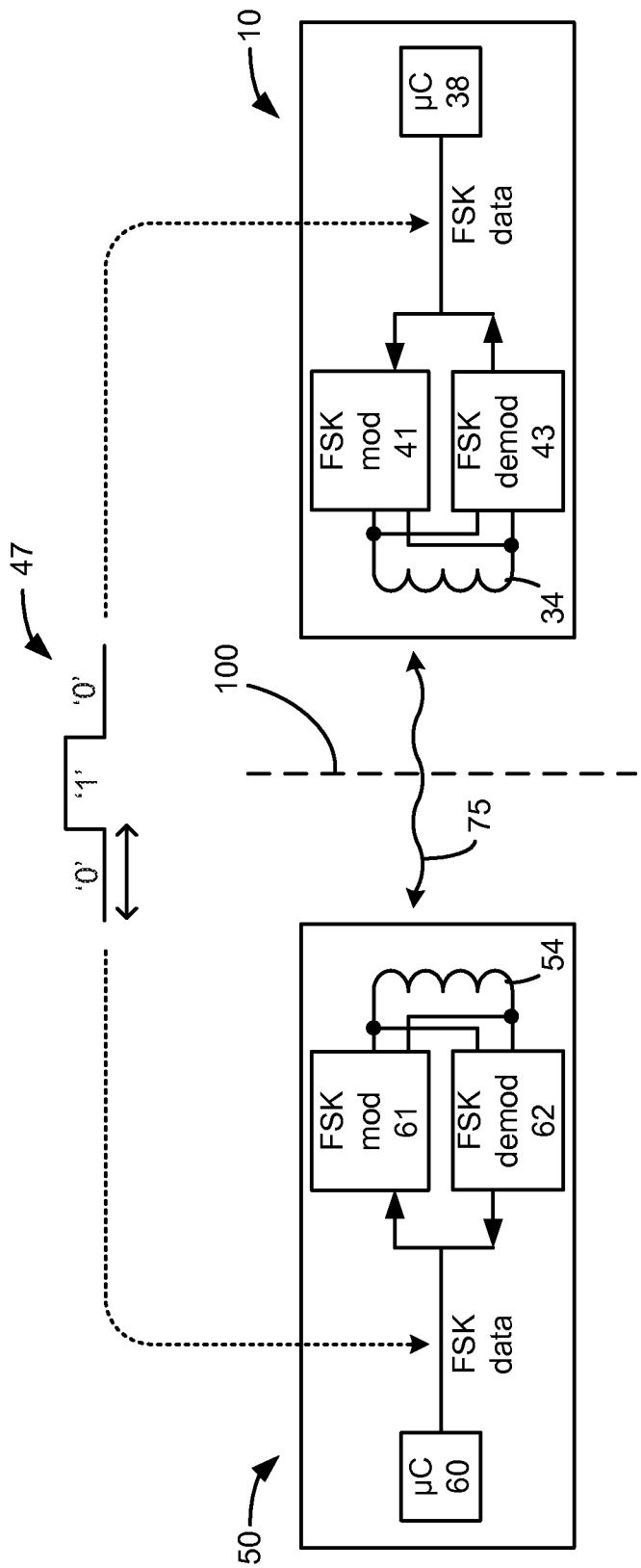
FIG. 3 shows the communication circuitry in the external controller and the IPG in accordance with the prior art.
Figure 5:
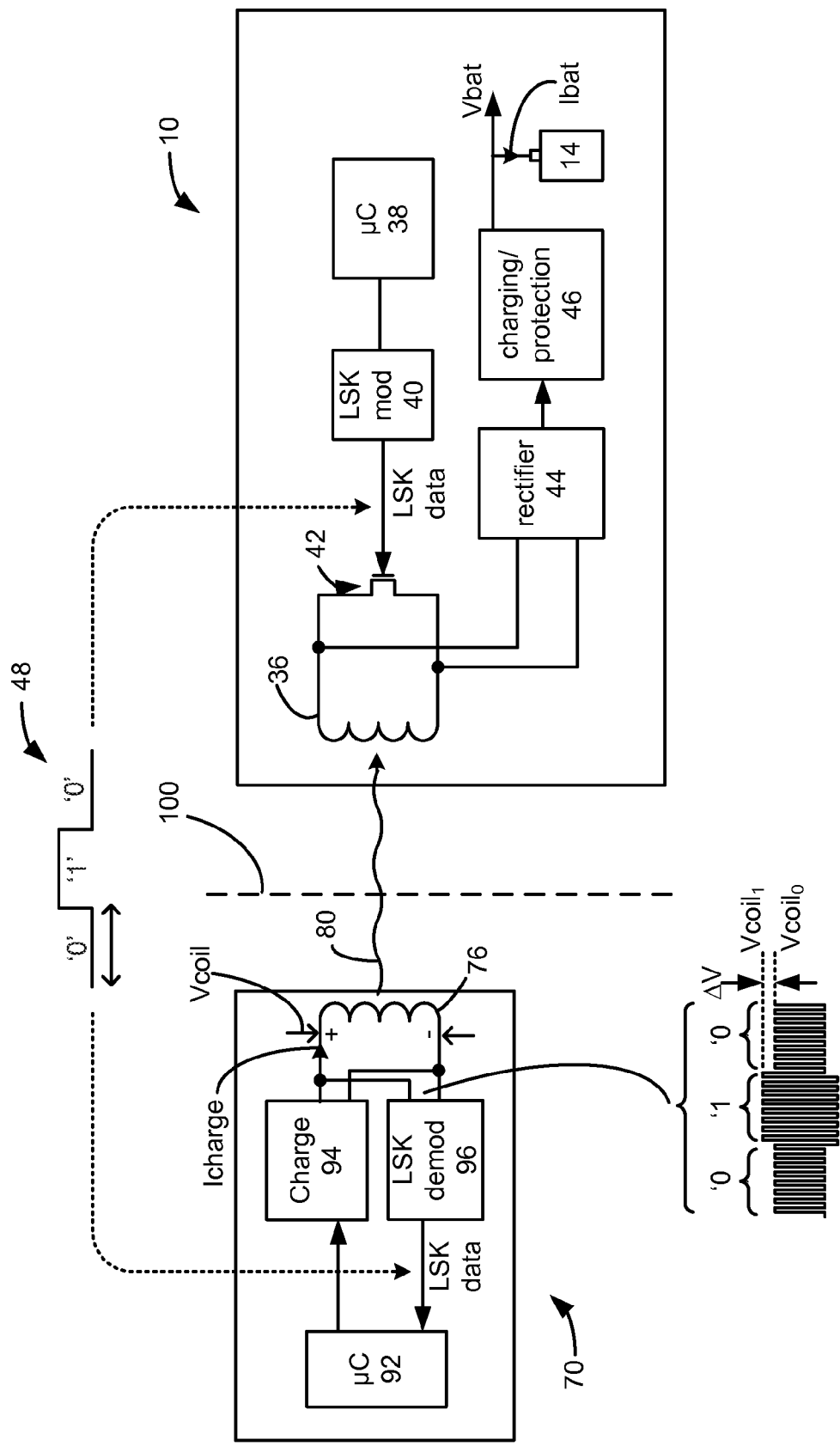
FIG. 5 shows the communication circuitry in the external charger and the IPG in accordance with the prior art.
Figure 6B:
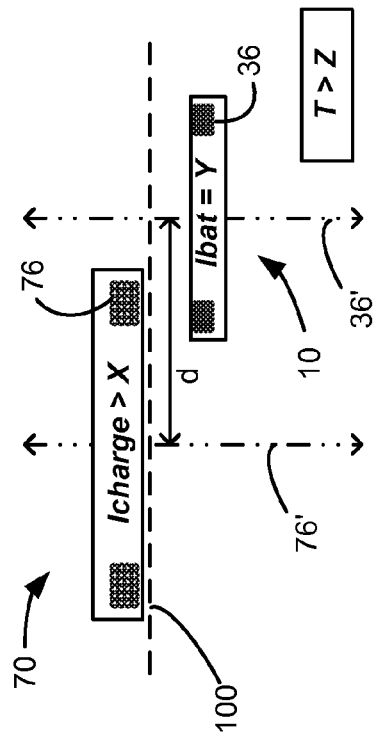
FIGS. 6A-6D show different alignment scenarios between the external charger and the IPG in accordance with the prior art.
Figure 6D:
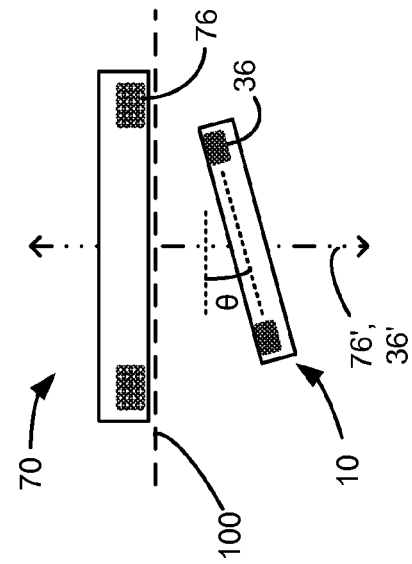
Figure 6A:
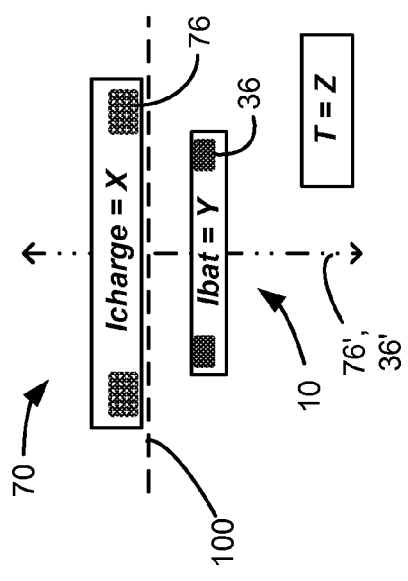
Figure 6C:
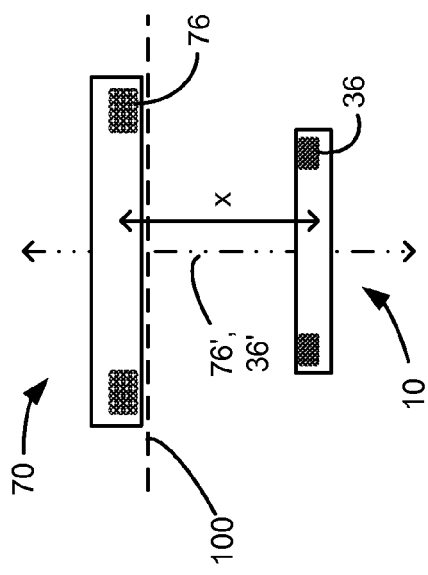
Figure 12:
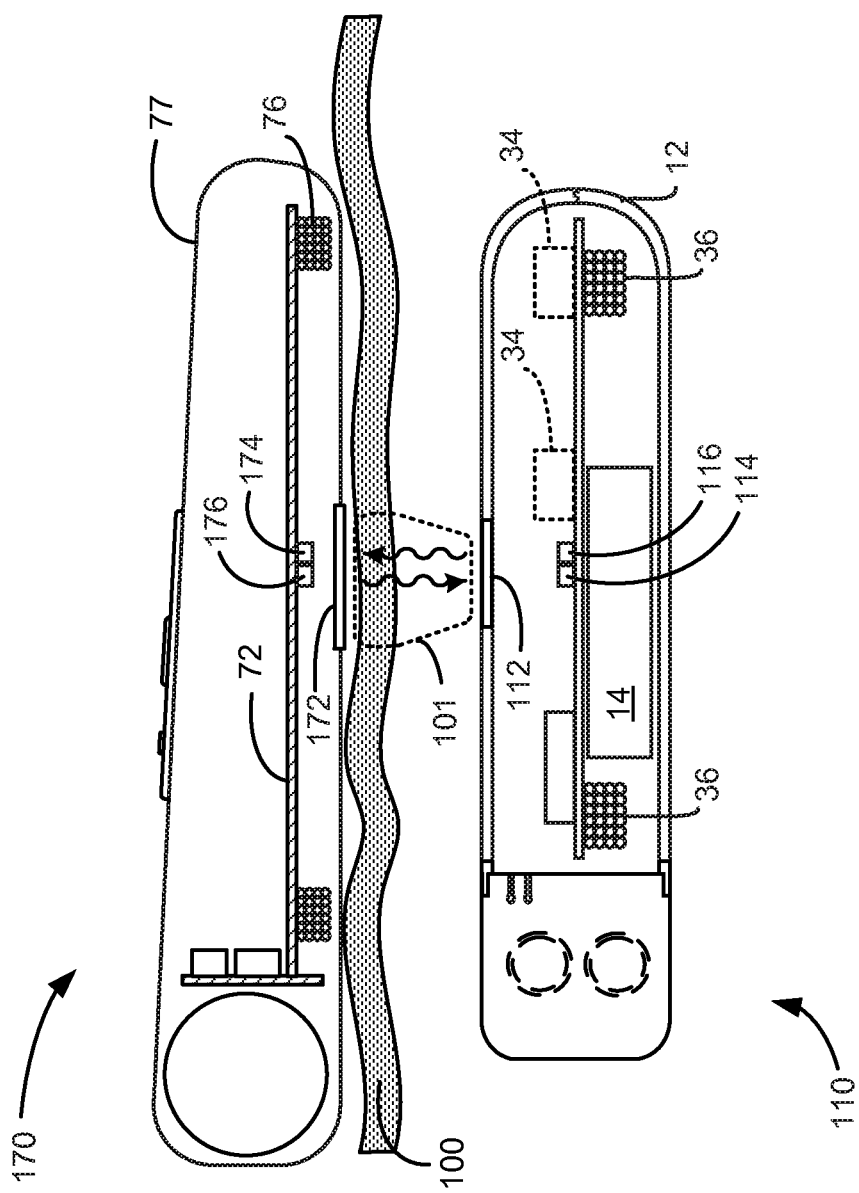
FIG. 12 shows an improved external charger for communicating with the improved IPG.

Through-the-skin visual feedback can also be used to indicate information relevant to the battery 14 in the IPG 110, such as when it needs to be recharged. In one simple example illustrated in FIG. 6A, the photoemitter 114 may pulse 102 when charging is required (when Vbat is low. More complicated visible feedback scenarios are also possible, such as changing the pulse frequency (f) as a function of Vbat. Such pulses 102 can be of constant intensity (I) over their pulse width (pw), or could also include modulated data interpretable by the external controller 150 (FIG. 9) or the external charger 170 (FIG. 12). For example, pulses 102 could include data such as an instruction to the external charger 170 start charging and/or the level of the battery 14 (Vbat). Pulses 102 could also include error codes interpretable by the external controller 150, which the patient could review on that device's graphical user interface. Such data modulation within pulses 102 may occur on a time scale not visually resolvable by the patient, who instead may simply see single pulses 102 despite the data included within them.

Data-modulated portions of pulses (if any), may be small compared to the pulse width of the pulses, and can occur at the end or beginning of such pulses, or may be interleaved with pulses of constant intensity. Although the pulses 102 are shown as periodic, they don't have to be. Moreover, using photoemitter 114 in the IPG 110 to produce visual feedback, or pulses 102 specifically, is not strictly required.

FIG. 9 shows an improved external controller 150 operable to optically communicate with the improved IPG 110, which in this example comprises modifications to the external controller 50 disclosed earlier (FIG. 2A). Like the external controller 50 described earlier, external controller 150 is used to set or adjust the therapy settings the IPG 110 will provide to the patient, and to receive relevant data from the IPG 110.

External controller 150 includes an optical window assembly 163 formed in the bottom of its case 59 that will face inwardly of a patient during a communication session between the external controller 150 and the IPG 110. External controller 150 further includes a photoemitter 164 and a photodetector 166 affixed to its PCB 51 which are generally centered with the window assembly 172. As with the IPG 110, external controller 150 may have only one of photoemitter 164 or photodetector 166 in a uni-directional application. Because the external controller 150 is not governed by the same hermeticity requirements as the IPG 110, the manner in which the window assembly 172 is affixed to a hole in the case 59 is less critical, and can occur in any manner suitable for an external device.

Moreover, the photoemitter 164' and photodetector 166' can also be modified to pass through one or more holes in the case 77, or photoemitter 164" and a photodetector 166" may be located outside of the case 77, with their lead wires passing through one or more smaller holes in the case, as shown in the bottom of FIG. 9. Coatings or epoxies can be useful to hold the photoemitters 164' or 164" the photodetectors 166' or 166' to the case 77 and for mechanical protection in these modification. Despite such modified placement of these optical devices of the external controller 150, the subsequent discussion focuses for simplicity on placement using a windows assembly 153, even though these modified placements could be used subsequently as well.

The photoemitter 164 and photodetector 166 in the external controller 150 may operate at the same wavelengths described earlier for the photoemitter 114 and a photodetector 116 in the IPG 110. Photoemitter 164, like photoemitter 164, will illuminate tissue 101 at a sufficient depth (x) to reach the optical window assembly 112 of the IPG 110. As such, at least some amount of the optical radiation from photoemitter 164 in the external controller 150 will reach the photodetector 116 in the IPG 110, and at least some amount of the optical radiation from photoemitter 114 in the IPG 110 will reach the photodetector 166 in the external controller 150. This allows the two devices 110 and 150 to bi-directionally optically communicate through the patient's tissue 100.

The window assembly 153 can appear anywhere on the external controller 150, but the window assembly 112 of the IPG 110 is preferably generally centered with its charging coil 36. This placement of window assembly 112 is useful if the IPG 110 is additionally charged by an external charger 170 (FIG. 12) that employs optical communications, as described below. Another place where the window assembly 153' and its corresponding photoemitter 164 and photodetector 166' may be placed on the external controller 150 is on its edge next to the port 58 (FIG. 2A) as shown in dotted lines, which may make accessing the user interface of the external controller 150 easier during a communication session with the IPG 110. As with the window assembly 112 of the IPG 110, the window assembly 153 could comprise a lens to better focus optical radiation emitted from photoemitter 164, or received at photodetector 166, and may be comprised of any material able to pass suitable amounts of optical radiation.

The window assembly 153 of external controller 150 preferably touches the patient's tissue 100 during a communication session in the center of the IPG 110, or at the illuminated tissue 101 if photoemitter 114 in the IPG 110 is providing visual feedback as discussed earlier. It is helpful to reduce ambient light in any space 149 between the external controller 150 and the tissue 100 that could otherwise interfere with optical communications, although if the optical devices in both are tuned to specific wavelengths, this is not as critical. Optical communications can still be had through a patient's clothing if it permits sufficient optical radiation to pass through.

Figure 10:
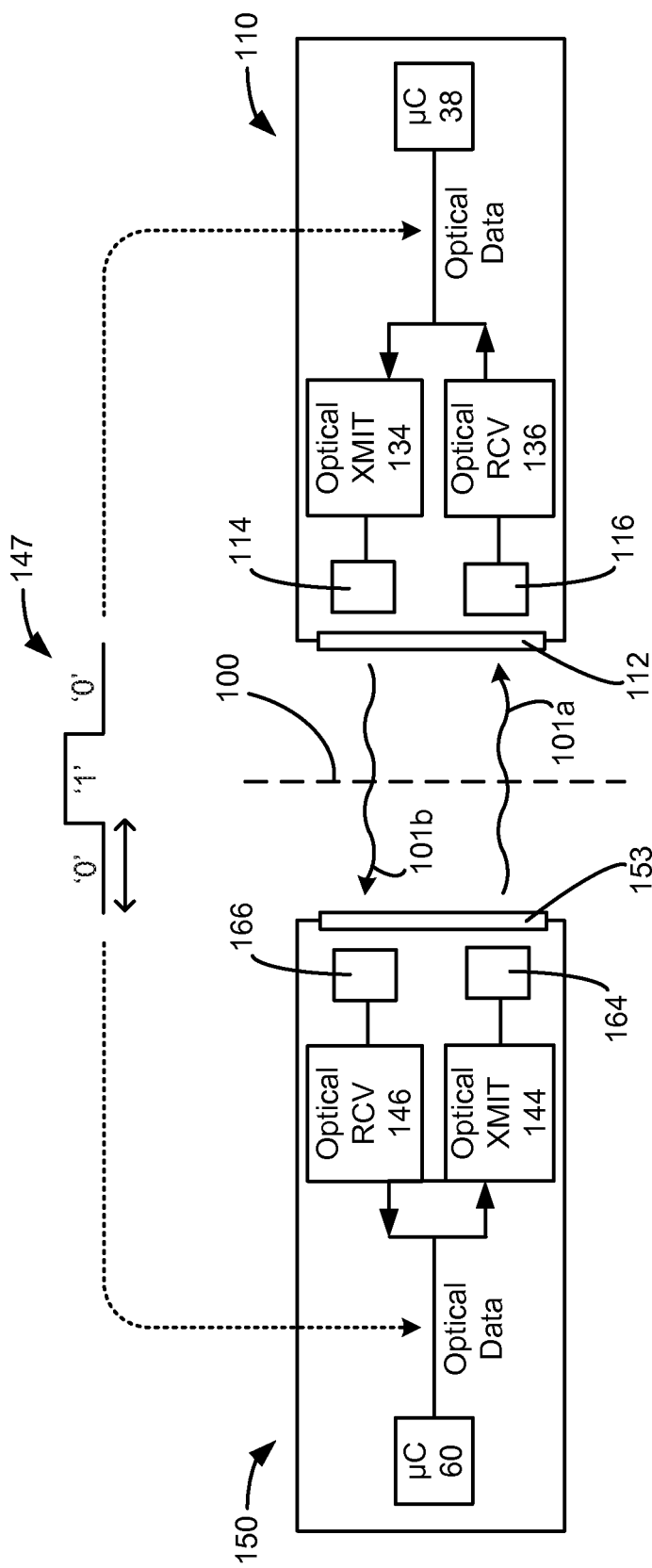
FIG. 10 shows the optical communication circuitry in the improved external controller and the improved IPG.

FIG. 10 shows circuitry that can be used for bi-directional optical communications between the external controller 150 and the IPG 110 via optical communication links 101a and 101b (comprising the illuminated tissue 101), which are used to optically transmit and receive a series of digital data bits 147. Such circuitry includes optical transmitters (144, 134) coupled to the photoemitters (164, 114) in the external controller 150, and optical receivers (146, 136) coupled to the photodetectors (166, 116) in the IPG 110. The optical transmitters 144 and 134 may include necessary modulation circuitry to convert the digital data bits 147 into appropriate modulated analog signals to drive the photoemitters 164 and 114 per the modulation scheme chosen. The optical receivers 146 and 136 may likewise include necessary demodulation circuitry to convert the modulated analog signals received at the photodetectors 166 and 116 into the series digital data bits 147 per the same modulation scheme.

The optical data modulation scheme used in the optical transmitters 144 and 134 can include Phase Shift Keying (PSK), which can occur at 9600 bits-per-second in one example. See, e.g., K. Inoue et al., "Transcutaneous Optical Telemetry System with Infrared Laser Diode," ASAIO J. at 841 (1998), which is submitted in the Information Disclosure Statement filed herewith. If PSK is used as the modulation scheme, the optical receivers 146 and 136 could comprise Phase Locked Loops (PLLs) for example. However, use of PSK modulation is merely one example. For example, Pulse Width Modulation (PWM), On-Off Keying (OOK), Differential Phase Shift Keying (DPSK), Pulse Amplitude Modulation (PAM), Quadrature Amplitude Modulation (QAM), M-ary varieties of the foregoing, etc., could also be used. The nature of optical communications would also allow for significant higher bit rates, although 9600 bits-per-second would generally be sufficient for communications between the external controller 150 and the IPG 110.

The optical receivers 146 and 136 in the external controller 150 and IPG 110 may not be strictly necessary, or could be modified. For example, if control circuitries 60 and 38 are additionally programmed to provide necessary demodulation functionality, the optical receivers 146 and 136 may comprise Analog-to-Digital (A/D) converters that can digitize the analog intensity signal provided by the photodetectors 176 and 116, and provide these digitized intensity values to their respective control circuitries 60 and 38 to determine the individual data bits. If the control circuitries 60 and 38 provide A/D inputs capable of digitizing the data, separate optical receivers 146 and 136 may not be necessary at all, and the control circuitries can be programmed to perform the demodulation. Likewise discrete optical modulators 144 and 134 may also be modified or may not be required if control circuitries 60 and 38 are additionally programmed to provide necessary modulation functionality, or if they include D/A outputs that can drive the photoemitters 114 and 164 directly.

The optical receivers 146 and 136 in the external charger 170 and IPG 110 can vary in design depending on whether what is important in received optical signals is modulated data (D), intensity (Ia), or both, which may also depend of the modulation scheme being used. For example, received intensity Ia would be important in modulation schemes employing amplitude modulation, and can be important if a received optical signal is of constant intensity and without data, as discussed further below. In this regard, the optical receivers 146 and 136 can also report such received intensities Ia to the control circuitries 60 and 38 along with any digital data. Received intensity may involve filtering or integrating the analog signal from the photodetectors 166 or 166 either before or after they are digitized, or may be gleaned by processing in the control circuitries 92 and 38.

Figure 11:
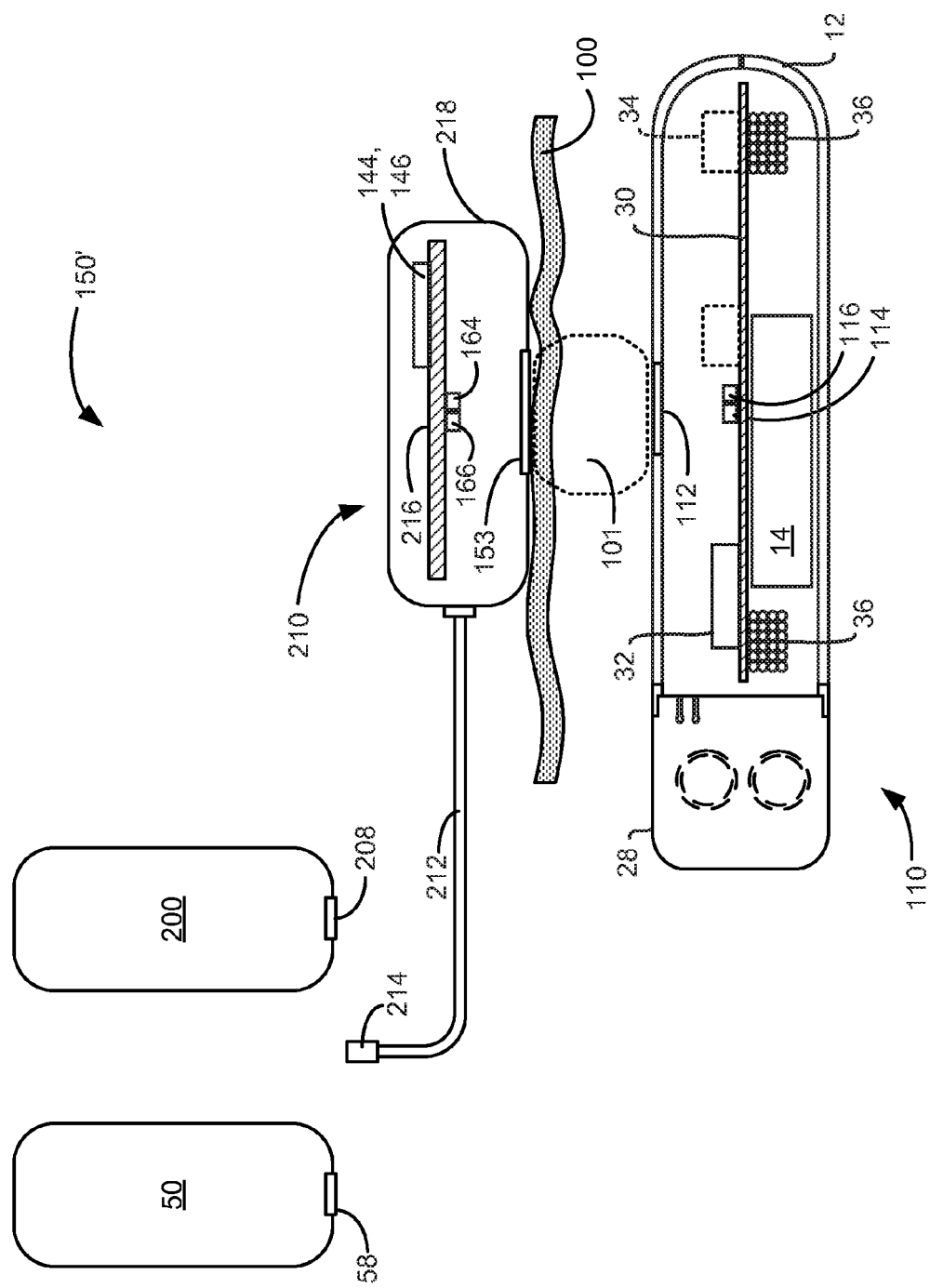
FIG. 11 shows a modified improved external controller having an optical communication head.

FIG. 11 shows another embodiment of an external controller 150' system that can optically communicate with IPG 110. In this example, optical components have been moved out of the external controller 150 (compare FIG. 9), and into an optical communication head 210, including the photoemitter 164, the photodetector 166, and if necessary, optical transmitter and receiver circuitry 144 and 146. These components may be integrated on a PCB 216, and contained within a housing 218, which may be significantly smaller and less complicated that the housing 59 used by the external controller 150. As shown, the optical communication head 210 includes a window assembly 153, similar to that described earlier for external controller 150, but could include the other optical device placement options discussed in FIG. 9.

The optical communication head 210 communicates with a mobile controller with a graphical user interface, such as the external controller 50 described earlier (FIG. 2A), or a mobile device 200 such as a cell phone, a tablet computer, or another hand-holdable portable control device. As depicted, the optical communication head includes a cable 212 and a connector 214 that can couple to appropriate ports 58 (FIG. 2A) or 208 on the mobile controller. However, such wired connection of the optical communication head 210 is not necessary, and instead it may communicate with the external controller 50 or mobile device 20 wirelessly using a suitable short-range protocol, such as Near Field Communication (NFC), Bluetooth, Bluetooth Low Energy (BLE), Wifi, Zigbee, etc, that is supported by the mobile controller. If such wireless communications were used, the optical communication head 210 may also additionally include a battery (as it could not receive power from the mobile controller by the cable 212), and telemetry circuitry compliant with the short-range protocol used. As disclosed in U.S. Provisional Patent Application Ser. No. 61/873,314, filed Sep. 3, 2013, and 61/874,863, filed Sep. 6, 2013, which are both incorporated herein by reference in their entireties, the mobile device 200 can include an executable application to provide a graphical user interface, which like external controller 50 can allow a patient to set or adjust the therapy settings the IPG 110 will provide to the patient, and to receive relevant data from the IPG 110.

Under control of the graphical user interface provided by the mobile controller, digital data bit to be transmitted to the IPG 110 can be serialized and sent to ports 58 or 208 and down the cable 212 to the head 210, or the data can be wirelessly transmitted from the mobile controller via a short-range protocol and recovered at the head 210. Once received at the head 210, the data is modulated at optical transmitter 144, with the modulated data driving photoemitter 144 in the head to provided optical data to the IPG 110 via link 101*a*. Optical data received from the IPG 110 via link 101*b* is received at photodetector 166 in the head 210, and is demodulated at optical receiver 146 to recover the series of digital data bits. Thereafter, the head 210 can provide the bits to the mobile controller via the cable 212, or wirelessly using the short range protocol. Note that providing optical transmitter and receiver circuitry 144 and 146 in the optical communication head 210 is not strictly necessary if the mobile controller can provide the proper signals at the ports 58 and 208 to drive and receive data from the photoemitter 164 and photodetector 166 directly.

The external controller 150' of FIG. 11, while having different pieces, may be more convenient for a patient, because it allows the optical communication head 210 to be placed proximate to the IPG 110 (such as in a belt with a pocket, or adhered to the patient's tissue 100 using double sided tape), while the mobile controller can remain relatively distant from the IPG 110 by virtue of the length of cable 212 or the length of the short-range protocol. This makes IPG optical communications easier, particularly if the IPG 110 is located in an area behind the patient, as occurs in an SCS application, as it permits the graphical user interface of the mobile controller to be held and seen in front of the patient. If the optical communication head 210 is held in place with a pouch, provisions can be made in the pouch to render it transparent to the optical radiation used to communicate between the head 210 and the IPG 110, such as by forming the patient-facing wall of the pouch with transparent plastic or a mesh material, by providing a hole in the patient-facing side for the optical window 153, etc.

The design of IPG 110 and external controllers 150 and 150' provide reliable means for optically communicating through the patient's tissue 100. The path optical communications take in the disclosed devices is direct compared to more-complicated prior art optical communication approaches discussed earlier. For example, when transmitting from the IPG 110 to the external controller 150, optical radiation generated at photoemitter 114 passes straight to a flat and relatively thin window 118 in window assembly 112 and thus will experience little attenuation in the IPG 110, as the optical radiation need not pass through curved or bulky translucent materials (like header 28) that can reflect or refract such radiation, or which contain additional components that could interfere with such radiation (such as feedthroughs, lead connectors, mirrors, etc.). The window assembly 112 is beneficially provided on a side of the IPG case that is already naturally facing outwardly of the patient when implanted, thus sending optical radiation trough the tissue 100 in a direct route out of the patient without re-direction and with little attenuation. After passing through the patient's tissue in this manner, the radiation again experiences little attenuation coming into the external controller 150, as it travels straight through another thin, flat window assembly 153 overlying photodetector 166, or directly to the photodetector 166 if alternatively mounted to the external controller 150 (see FIG. 9). Moreover, this optical communication path can be symmetric, as the window assemblies 153 and 112, the optical components, and their positions relative to the window assemblies can be essentially the same. These factors result in optical communications that can be transmitted with the same low levels of energy at both devices.

Discussion now turns to external charging, and to an improved external charger 170 that can optically communicate with the IPG 110. FIG. 12 shows the improved external charger 170, which includes an optical window assembly 172 formed in the bottom of its case 77 that will face inwardly of a patient during a charging session. External charger 170 further includes a photoemitter 174 and a photodetector 176 affixed to its PCB 72 which are generally centered with the window assembly 172, although again, only one of photoemitter 174 or photodetector 176 may be required in a uni-directional application. Because the external charger 170 is not governed by the same hermeticity requirements as the IPG 110, the manner in which the window assembly 172 is affixed to a hole in the case 77 is less critical, and can occur in any manner suitable for an external device. Moreover, the photoemitter 174 and photodetector 176 can be positioned through or on the bottom of case 77, as discussed with respect to the external controller 150 of FIG. 9, although these modifications are not again depicted for simplicity. Again, the window assembly 172 could comprise a lens to better focus emitted and received radiation, and may be comprised of any material able to pass suitable amounts of optical radiation.

The photoemitter 174 and photodetector 176 in the external charger 170 may operate at the same wavelengths described earlier for the photoemitter 114 and a photodetector 116 in the IPG 110. Photoemitter 174, like photoemitter 114, will illuminate tissue 101 at a sufficient depth (x) to reach the optical window assembly 112 of the IPG 110. As such, at least some amount of the optical radiation from photoemitter 174 in the external charger 170 will reach the photodetector 116 in the IPG 110, and at least some amount of the optical radiation from photoemitter 114 in the IPG 110 will reach the photodetector 176 in the external charger 170. This allows the two devices 110 and 170 to bi-directionally optically communicate through the patient's tissue 100.

The window assembly 172 can appear anywhere on the external charger 170, but is preferably generally centered with its charging coil 76 as shown. As will be discussed further below, this is useful in optically determining external charger/IPG alignment. It should however generally be easy for the patient to align the external charger 170 with the IPG 110 in preparation for a charging session. For example, if the patient sees pulses 102 (FIG. 8A) illuminating her tissue 101, this may indicate that the battery 14 in the IPG 110 is low, and that charging is required. The patient can thus visually place the window assembly 172 on the bottom of the external charger 170 over the illuminated tissue 101, as shown in FIG. 12. The external charger 170 generally touches the patient's tissue 100 during a charging session to reduce ambient light that could otherwise interfere with optical communications, as described earlier. As such, the external charger 170 will tend to block such ambient light, and as a result, a less-powerful photoemitter 174 and less-sensitive photodetector 176 may be used in external charger 170 when compared to such optical devices in the external controller 150 described earlier. Optical communications can still be had with the external charger 170 through a patient's clothing or using a modified pouch as described earlier.

Figure 13:
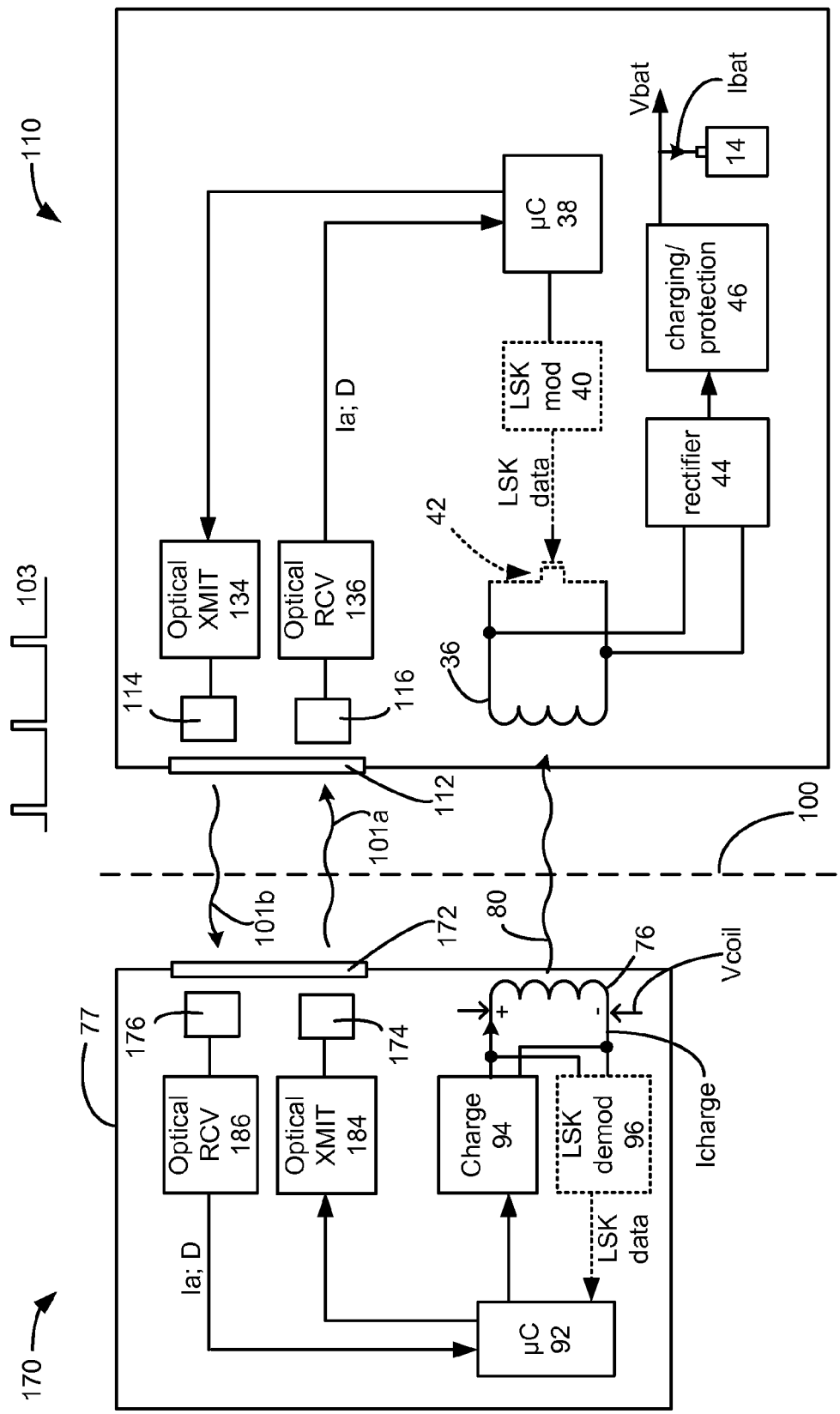
FIG. 13 shows the optical communication circuitry in the improved external charger and the improved IPG.

FIG. 13 shows circuitry that can be used for bi-directional optical communications between the external charger 170 and the IPG 110 via optical communication links 101*a* and 101*b* (comprising the illuminated tissue 101), which includes optical transmitters (184, 134) coupled to the photoemitters (174, 114), and optical receivers (186, 136) coupled to the photodetectors (176, 116). The optical data modulation scheme used in the optical transmitters 184 and 134 can again include Phase Shift Keying (PSK) or any of the other modulation schemes mentioned earlier with respect to the external controller 150. In short, the optical components in the external charger 170 can largely mimic those appearing in the external controller 150 described earlier.

The external charger 170 and IPG 110 can communicate optically whether or not the external charger 170 is producing a magnetic changing field 80 to charge the IPG 110's battery 14 during a charging session. This is in distinction to LSK communications, which as noted earlier can only occur while the magnetic charging field 80 is produced. Moreover, optical communications will not interfere with the magnetic charging field 80 and so can occur during a charging session, unlike systems that use EM telemetry schemes to determine alignment that were discussed earlier.

The external charger 170 and IPG 110 can optically communicate for many useful reasons. For example, the IPG 110 can send an optical signal with data via link 101b to instruct the external charger 170 to start generating a magnetic charging field 80 or to send the battery voltage Vbat, which as already noted may be included in pulses 102 (FIG. 8A). Other examples of optical communications along link 101b are discussed in detail below.

The external charger 170 can also optically communicate data to the IPG 110 along link 101a. For example, the external charger 170 when positioned over the IPG 110 can optically send an instruction to the IPG 110 to report its battery capacity, Vbat, along link 101b, which may be beneficial if pulses 102 are not used to indicate Vbat, or if pulses 102 are merely of constant intensity and do not contain data such as Vbat. Once Vbat is then optically reported from the IPG 110 to the external charger 170, the external charger 170 can initiate a charging session by generating a magnetic charging field 80 if necessary (i.e., if Vbat is low). Alternatively, the external charger 170 may optically send further instructions to the IPG 110 via link 101a informing the IPG 110 of the desired to begin charging, with such charging commencing only after the external charger 170 optically receives an acknowledgement from the IPG 110 via link 101b. This might be desired to allow the IPG 110 time to prepare itself for charging. Link 101a can also be used during a charging session. For example, the external charger 170 might periodically provide information to the IPG 110 during the charging session, such as an estimation of how much longer the external charger 170 believes charging may last. Alternatively, the external charger 170 may not have a photoemitter 174, and thus may only allow for one-way optical communications from the IPG 110 (via link 101b).

Once the IPG 110 starts receiving the magnetic charging field 80, it preferably periodically optically sends data to the external charger 170 via link 101b, which is shown in FIG. 13 as pulses 103. Pulses 103 may be the same as pulses 102 (FIG. 8A), which may simply continue after receipt of the magnetic charging field 80, and which may now contain additional data relevant to the charging session. Pulses 103 may include for example the IPG's battery voltage (Vbat), the temperature of the IPG (T), information indicative of the electrical coupling between the external charger 170 and the IPG 110 such as the battery charging current (Ibat), or all of these or still other parameters relevant to the current charging session. Again, although pulses 103 are shown as periodic, they don't have to be, so long as they are sent with a suitable frequency to allow the external charger 170 to optically receive data on a reasonable time scale during the charging session (e.g., every second).

The external charger 170 may use such optically-received data to control the magnetic charging field 80 it is producing. For example, if the external charger 170 understands that the optically-reported temperature data (T) from the IPG 110 is above a threshold for example, it can reduce the energy of the magnetic charging field 80, for example by lowering Icharge, or by reducing the duty cycle of the field. See, e.g., U.S. Patent Application Publication 2011/0087307. The external charger 170 can also monitor optically-reported coupling data (e.g., Ibat), and adjust the magnetic charging field 80 accordingly, for example by increasing Icharge or the duty cycle if Ibat is lower than a threshold, or by reducing these magnetic charging field parameters if Ibat is higher than a threshold. Monitoring optically-reported data for Vbat may also be used by the external charger 170 to control the magnetic charging field 80 or to monitor the progress of charging generally, as well as to understand when Vbat is fully charged (e.g., to a threshold), so that generation of the magnetic charging field 80 can cease.

Figure 14A:
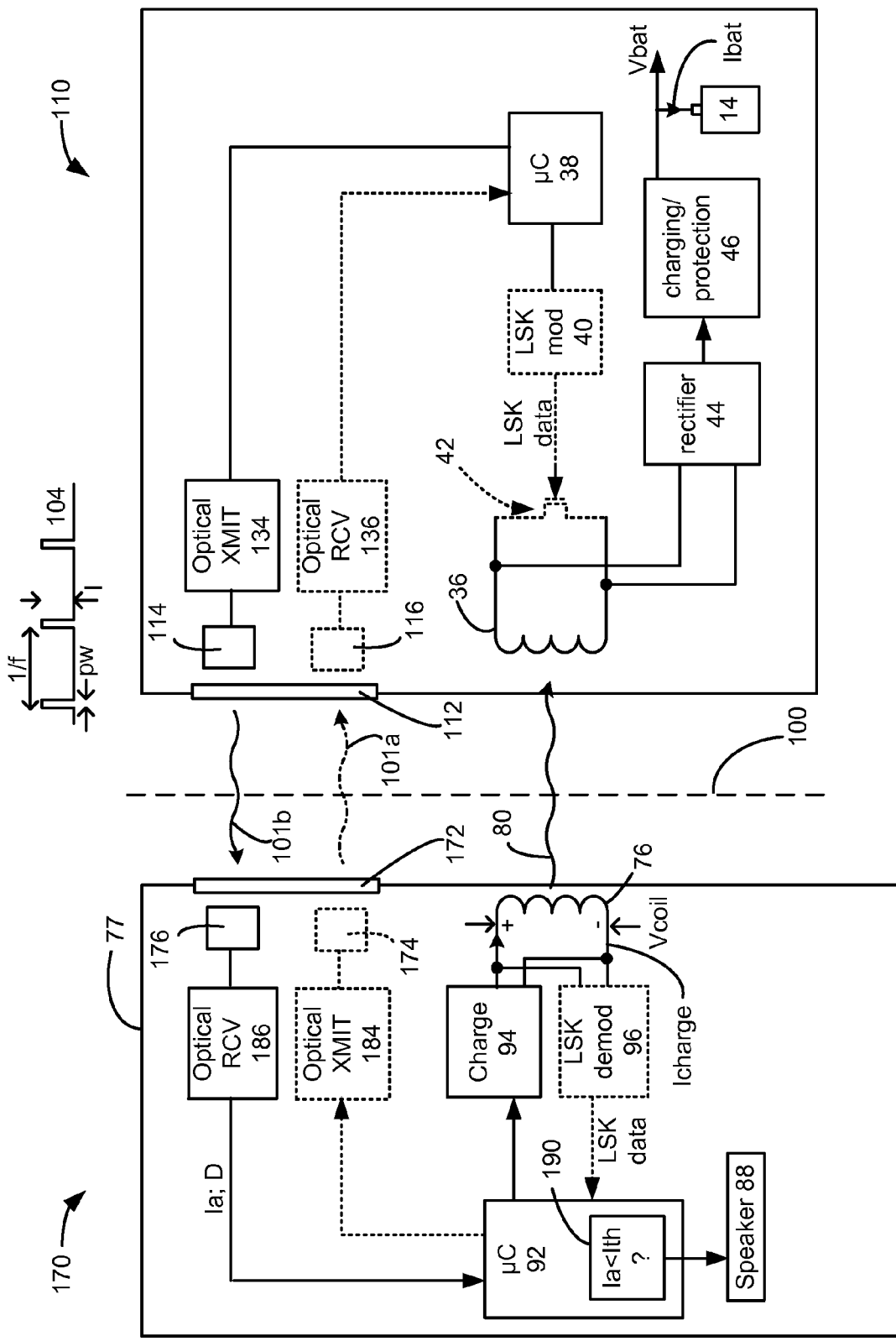
FIGS. 14A-14C show use of the optical communication circuitry to determine external charger/IPG alignment.

Optical communications can also be used in determining external charger 170/IPG 110 alignment, which as noted earlier is important to ensure fast IPG battery charging without overheating. Additional circuitry is shown in FIG. 14A to assist with the determination of alignment, including an alignment detector, which in the example shown comprises an intensity module 190 programmed in the external charger 170's control circuitry 92. In this example, alignment is determined by assessing the received intensity (Ia) of optical signals transmitted by the photoemitter 114 in the IPG 110, and detected at the photodetector 176 in the external charger 170 via optical link 101b. Optical receiver 186 in the external charger 170 can be configured to provide the received intensity, Ia, as describer earlier in conjunction with the external controller 150.

These optical signals are shown as alignment pulses 104 in FIG. 14A, and can comprise the same pulses 102 or 103 discussed earlier, and thus may contain modulated data (D). If the pulse width (pw) of pulses 104 is relatively large compared to portions that might contain optically-modulated data, the presence of such data in pulses 104 should not affect their received intensities, Ia. Alternatively, pulses 104 may comprise pulses of constant intensity over its pulse width. Pulses 104 can also be discrete from pulses 103 (FIG. 13), and may be interleaved with these pulses during a charging session. As with earlier pulses, pulses 104 do not have to be periodic, but are preferably sent with a suitable frequency to allow the external charger 170 to receive data on a reasonable time scale to assess alignment in real time from the patient's perspective (e.g., every second).

In this example, the photoemitter 114 in the IPG 110 issues optical pulses 104 during a charging session of a known intensity, I. As the pulses 102 pass through the illuminated tissue 101 (101b), they will attenuate, and thus will be received at the external charger 170 with a lower intensity, Ia. This intensity Ia can be determined at the optical receiver 186 in the external charger 170 as explained earlier.

Figures 14B, 14C:
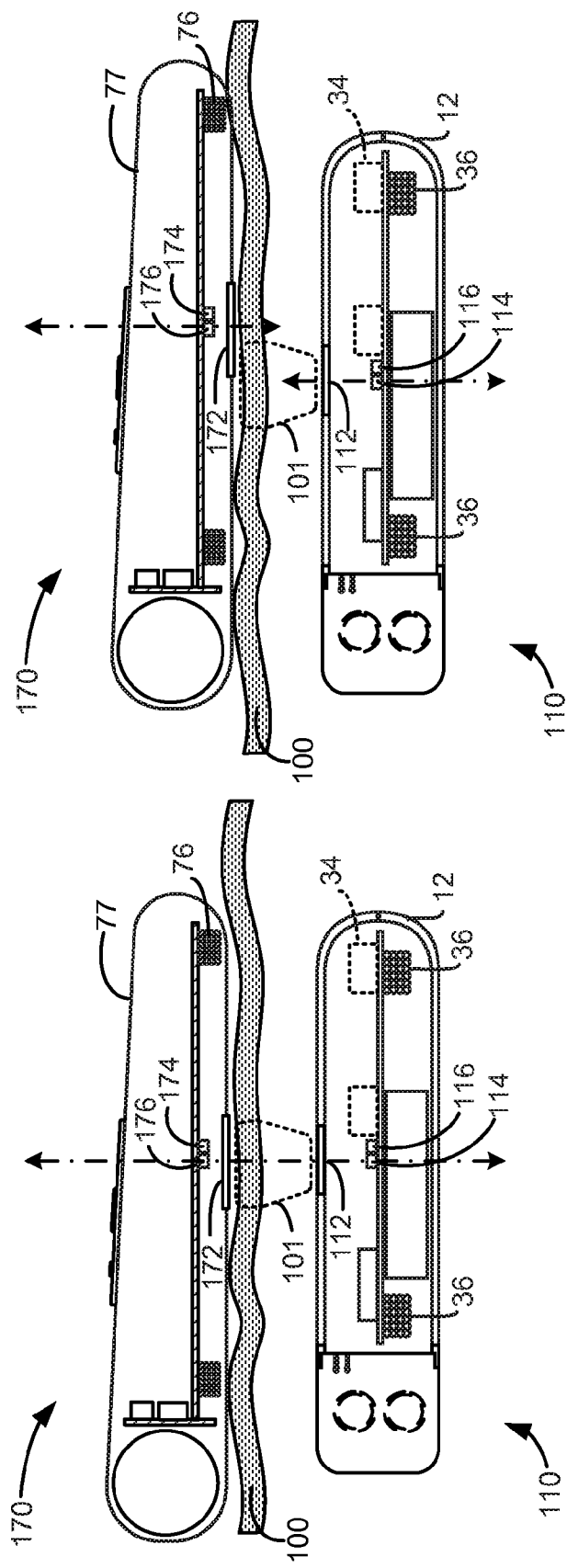

Once Ia is received, it is presented to intensity module 190, which compares Ia to an intensity threshold, Ith, to determine if Ia is lower than it should be, which may warrant a conclusion that the external charger 170 is misaligned with respect to the IPG 110. FIGS. 14B and 14C show the effect of external charger 170/IPG 110 alignment on received optical intensity, Ia. In FIG. 14B, the external charger 170 and IPG 110 are well aligned, and the axes through their window assembly 172 and 112 are collinear. Because the window assemblies 172 and 112 are also generally centered with respect to charging coils 76 and 36 respectively, these coils 76 and 36 are thus also collinear, which as noted earlier (FIG. 6A) represents good alignment and electrical coupling between the external charger 170 and IPG 110. When well aligned, the window assembly 172 of the external charger will cover a broader area of the tissue 101 illuminated by the photoemitter 114 in the IPG 110, and thus the photodetector 176 in the external charger 170 will receive a larger amount of optical radiation (i.e., Ia>Ith), and thus Ia will be relatively high.

By contrast, in FIG. 14C, the window assembly axes and the charging coils are not collinear; the window assembly 172 covers a smaller area of the illuminated tissue 101; photodetector 176 receives a smaller amount of optical radiation; and Ia is relatively low (e.g., Ia<Ith), indicating poor alignment and coupling. Should the intensity module 190 detect this condition, it can notify the patient of the misalignment condition using speaker 88 as described earlier so that the patient can readjust the position of the external charger 170.

An IPG can be implanted at different depths (x; FIG. 8A) in different patients, and so the received intensity Ia may vary from patient to patient. Thus, the intensity threshold, It, is preferably established for a given patient during a training or learning phase. For example, when first using the external charger 170, a patient may be instructed to very carefully align the two window assemblies 172 and 112, to press the external charger 170 firmly against her tissue 100, and to turn on the external charger 170 to start generating a magnetic charging field 80. The external charger 170 can then assess the strength of Ia for this known good alignment condition, and then set Ith in the intensity module 190 at an appropriate lower value.

Figure 15B:
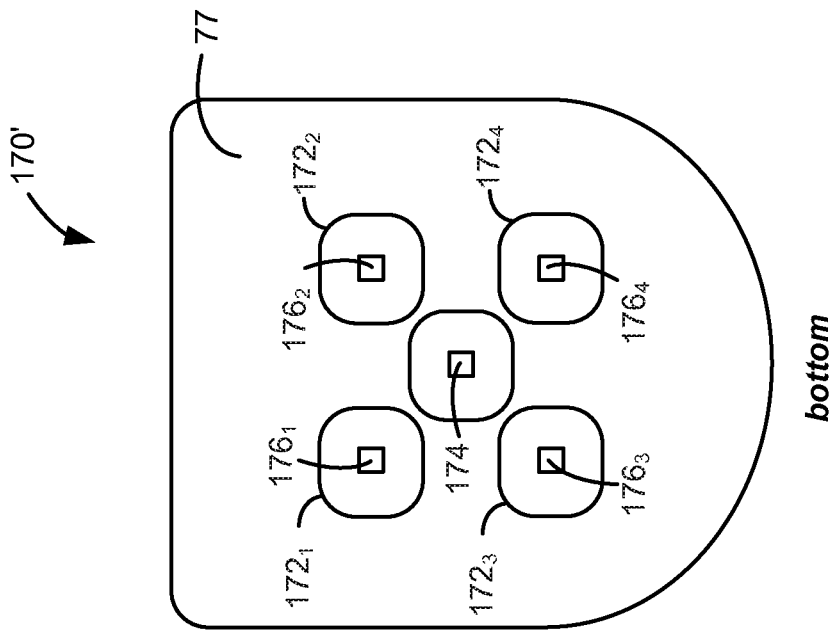
FIGS. 15A-15D show use of the optical communication circuitry to determine a direction of external charger/IPG misalignment.
Figure 15A:
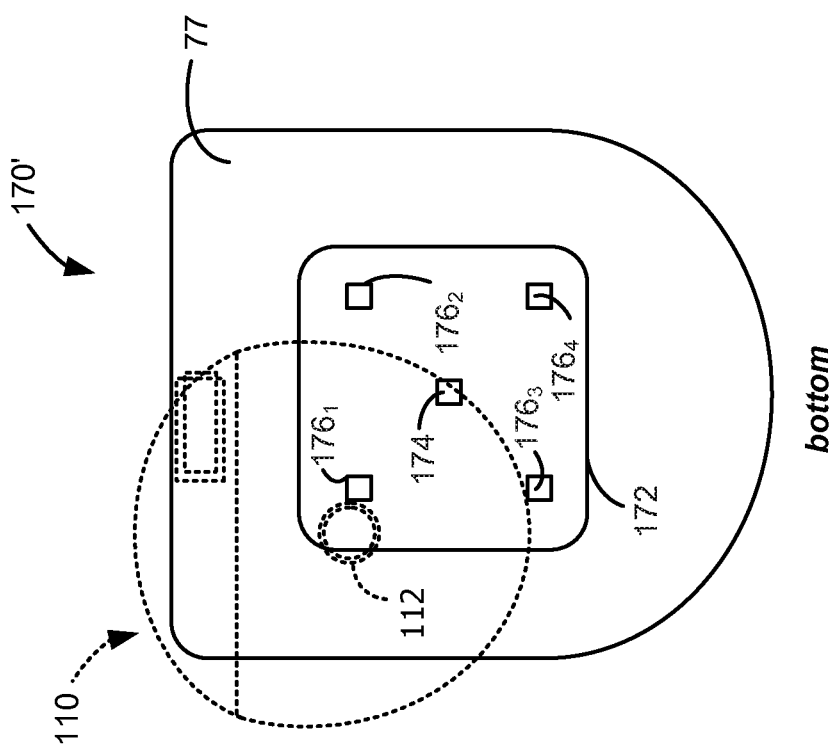

FIGS. 15A-15D illustrate a different embodiment of an external charger 170' that as well as determining alignment optically can also determine a direction in which the external charger 170' is misaligned with respect to the IPG 110, and indicate this to the patient to assist in adjustment. In FIG. 15A, the bottom side of the external charger 170' includes a larger window assembly 172, and mounted to the PCB 72 are a number of photodetectors $176_k$ arranged radially around a central photoemitter 168, and also arranged radially with respect to the charging coil 76 (FIG. 7). FIG. 15B shows the photodetectors $176_k$ at the same locations, but with each having its own window assembly $172_x$ in the external charger's case 77. A central photodetector could also be present at the central location of the photoemitter 174 to assist in communications or alignment as described earlier, but this is not shown.

In either example, the photodetectors $176_k$ will receive different intensities $Ia_x$ from the central photoemitter 114 in the IPG 110 depending on external charger 170'/IPG 110 alignment. An underlying IPG 110 is shown in dotted lines in FIG. 15A to illustrate this. Notice that photodetector $176_1$ is relatively aligned with the window assembly 112 and photoemitter 114 in the IPG 110, and thus will receive a relatively strong intensity $Ia_1$. Photodetectors $176_2$ and $176_3$ are more distant, and will receive smaller intensities $Ia_2$ and $Ia_3$. Photodetector $176_4$ is far away from the IPG window assembly 112, and thus will receive a small intensity $Ia_4$, which may be zero.

Figure 15C:
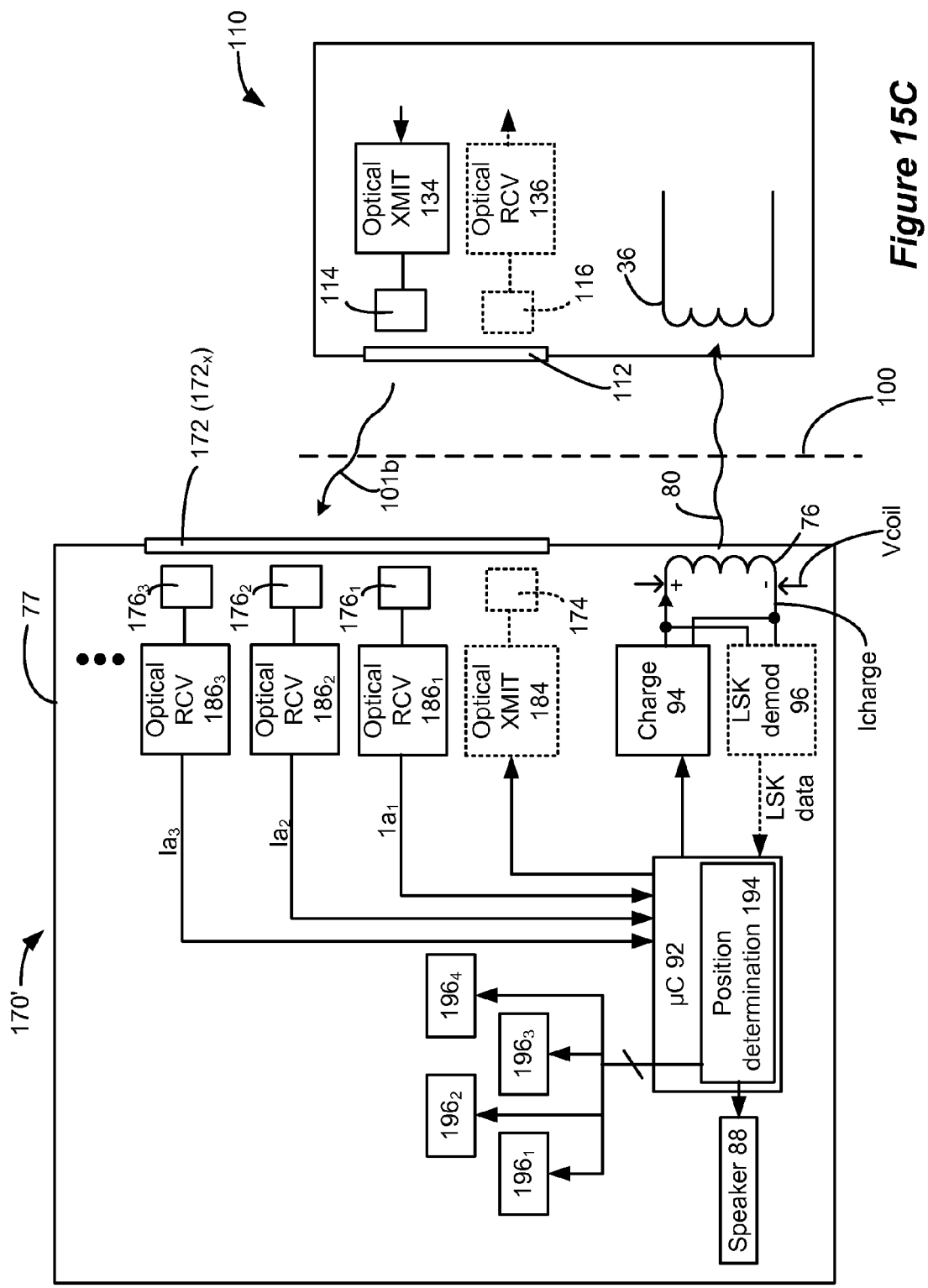

As shown in FIG. 15C, optical receivers $186_x$ corresponding to the photodetectors $176_x$ in the external charger 170' report these intensity values $Ia_x$ to the control circuitry 92. Although separate optical receivers $186_x$ are shown, a single optical receiver 186 could also be used to sample the received intensities $Ia_x$ from the various photodetectors $176_x$ at different points in time.

The control circuitry 92 is programmed with a position determination module 194 that assesses the reported intensities $Ia_x$ to triangulate the position of the external charger 170' with respect to the IPG 110, and to indicate misalignment to the patient. Such misalignment indication can include use of the speaker 88 as discussed earlier, but in addition direction indicators $196_x$ are used to inform the patient in which direction the external charger 170' should be moved to improve alignment and electrical coupling with the IPG 110 during the charging session. These direction indicators $196_x$ in one example can comprise LEDs on the top face of the external charger 170' that may (but need not) generally coincide with the location of the photodetectors $176_x$ as shown in FIG. 15D.

Figure 15D:
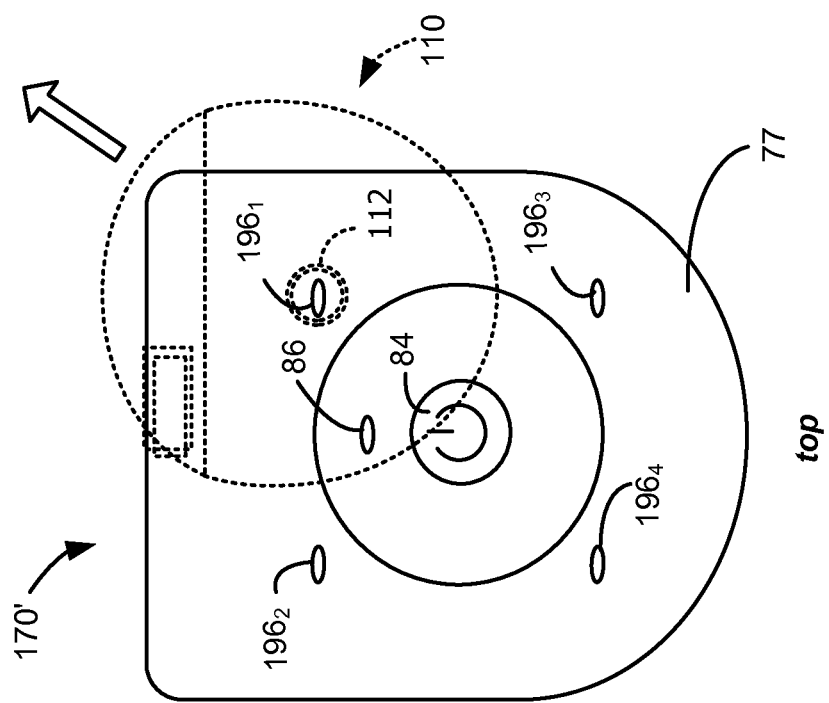

Continuing the example misalignment condition of FIG. 15A in FIG. 15D, upon determining that the photoemitter 114 in IPG 110 is near photodetector $176_1$, somewhat near photodetectors $176_2$ and $176_3$, but far from photodetector $176_4$, the position determination module 194 may light LED $196_1$ with a strong brightness, LED $196_2$ and $196_3$ with a moderate brightness, and $196_4$ with a low brightness, to indicate the direction that the patient should move the external charger 170', i.e., to the north-east as shown by the arrow in FIG. 15D. In other words, the position determination module 194 can control the direction indicators $196_x$ in accordance with the receive intensities values $Ia_x$, and may do so in manners other than by controlling their brightness, such as by pulse rate or color. If alignment pulses 104 are provided frequently enough to the external charger 170', control of the LEDs 196 by the position determination module 194 can occur in essentially real time to allow a patient to visually assess their progress toward achieving better alignment as she moves the external charger 170' by viewing the LEDs.

Once suitably aligned, none of the LEDs $196_x$ may be lit, at which time indications from the speaker 88 might also cease. Enablement or disablement of the speaker 88 though need not coincide with enablement or disablement of the LEDs $196_x$, and instead use of the speaker may be limited to gross misalignment conditions, for example, when no photodetector 176 in the external charger 170' is receiving a suitable level of intensity $Ia_x$. Speaker 88 may also be dispensed with.

Because the disclosed optical techniques for determining and indicating external charger/IPG alignment do not depend on electrical measurements taken during production of a magnetic field 80, the techniques may be used prior to a charging sessions, i.e., prior to use of the external charger 170 to produce a magnetic charging field 80. This is beneficial, as it allows a patient to set the positioning of the external charger 170 before the charging session begins, which hopefully the patient would not need to revisit later during the charging session. However, should alignment change during the charging session, the disclosed techniques can still notify the user and to suggest corrections, as explained above.

It should also be noted that the optical alignment techniques described above (FIG. 14A-15D) with respect to the external charger 170 (FIG. 14A-15D) can also be used with the external controllers 150 and 150'. This may be beneficial to ensure good optical coupling, and hence reduced optical attenuation, between the two before or during the communicating data. The disclosed optical alignment techniques may also be used in conjunction with the prior art alignment techniques described earlier. For example, the prior art techniques can be used to enable coarse alignment between the external device and the IPG 110, with the disclosed optical techniques then used for fine alignment assessment and adjustment.

Figure 16:
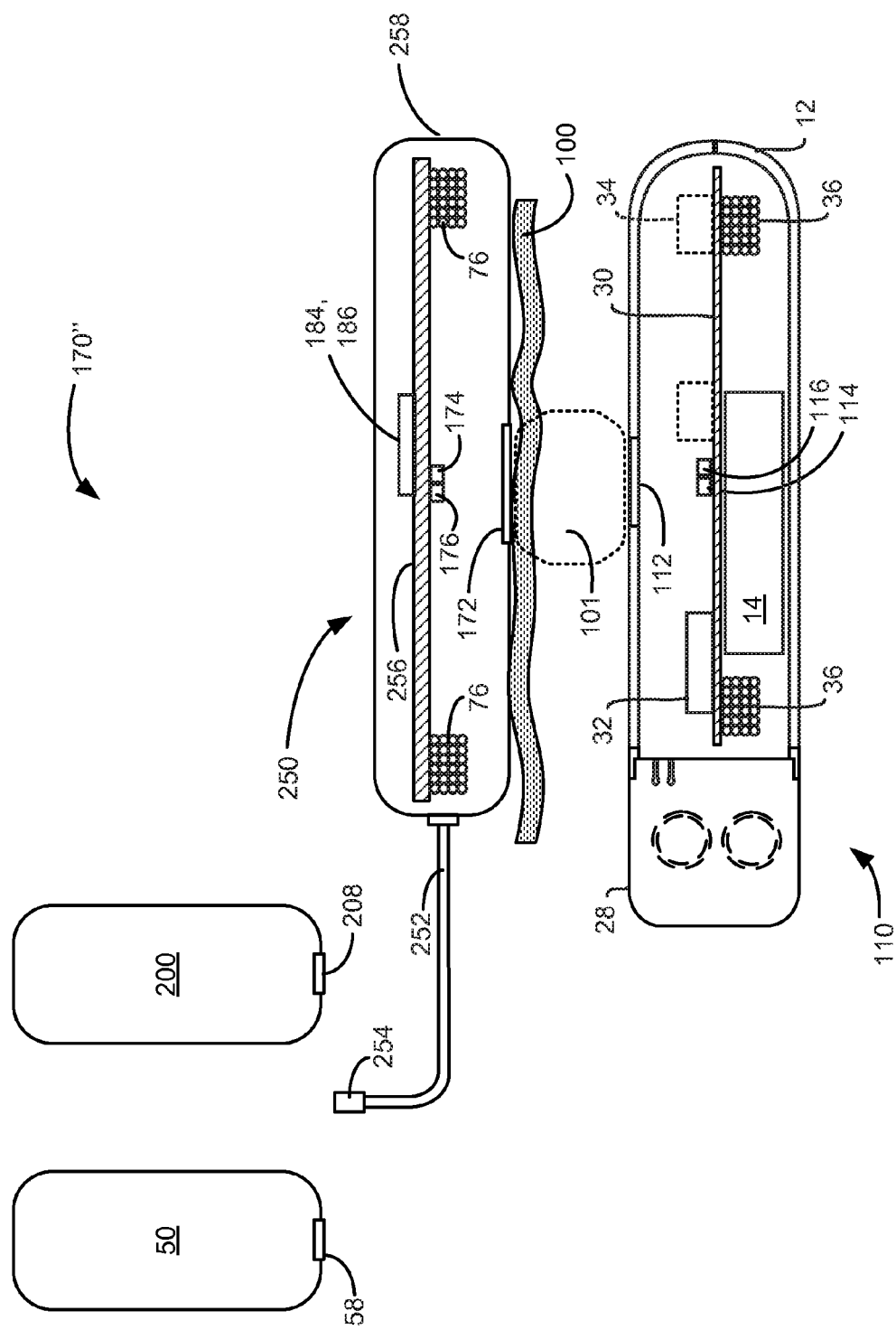
FIG. 16 shows a modified improved external charger having a charging head with optical communication capabilities.

FIG. 16 shows another embodiment of an external charger 170" system that can optically communicate with IPG 110. In this example, optical components have been moved out of the external charger 170 (FIG. 12), and into a charging head 250, including the photoemitter 174, the photodetector 176, and if necessary, optical transmitter and receiver circuitry 184 and 186. The charging head also includes the charging coil 76. These components may be integrated on a PCB 256, and contained within a housing 258, which may be significantly smaller and less complicated that the housing 77 used by the external charger 170. As shown, the charging head 250 includes a window assembly 172, similar to that described earlier for external charger 170 but could include the other optical device placement options discussed in FIG. 9. The window assembly 172 and optical devices 176 and 174 are preferably centered within the charging coil 76 in the head, which as noted earlier assists with determining alignment between the charging head for the same reasons discussed earlier. Charging head 250 could also include different photodetectors $176_x$ to allow for misalignment position determination, and could include direction indicators $196_k$ (see FIGS. 15A-15D), but this is not shown for convenience.

The charging head 250 communicates with a mobile controller such as the external controller 50 (FIG. 2A) or mobile device 200 as discussed earlier (see FIG. 11), or an external charger 70 (not shown). As depicted, the charging head 250 includes a cable 252 and a connector 254 that can couple to appropriate ports 58 or 208 on the relevant external device, which can provide a graphical user interface providing functionality similar to the user interface 82 of the external charger 70 (FIG. 4A), as described previously. Power for the charging head 250, as well as to generate the magnetic charging field 80 from the charging coil 76, can come from the external device via cable 252.

The external charger 170" can otherwise operate similarly with the external chargers 170 and 170' described earlier to optically communicate relevant charging information, and to allow the external device to determine charging head 250/IPG 110 alignment using such optical communications. The graphical user interfaces of the external device are further useful in that they can provide indications of misalignment (either using their speakers, or by displaying information on their graphical user interfaces). If the charging head 250 has multiple photodetectors $176_k$ allowing for misalignment direction assessment (see FIGS. 15A-15D), the direction indications concerning how to move the charging head 250 for better alignment can be displayed on the graphical user interfaces of these devices, essentially taking the place of LEDs $196_k$ in FIG. 15D.

The external charger 170" of FIG. 11, while having different pieces, may be more convenient for a patient, because, like optical communication head 210 (FIG. 11), it allows the charging head 250 to be placed proximate to the IPG 110 to allow optical communications and wireless charging to take place, while the external device can remain relatively distant from the IPG 110 by virtue of the length of cable 252, making it easier to access.

The design of IPG 110 and external chargers 170, 170' and 170" provided reliable means for optically communicating through the patient's tissue 100, and the same benefits discussed earlier for external controller/IPG communications apply here as well.

Optical communications between the IPG 110 and the external controller may render certain aspects of the prior art IPG 10 and external controller 50 unnecessary. For example, as FSK communications are not used, FSK modulation and demodulation circuitry (FIGS. 3, 41, 43, 61 and 62) as well as telemetry coils 34 and 54 are not necessary, and these coils are thus shown in dotted lines in IPG 110 and the various external controllers in recognition of this fact. This is significant, as coils 34 and 54 take up room in their respective, which may now be made smaller when optical communications are employed. Eliminating the telemetry coil 34 from the IPG 110 is particularly beneficial, as space is at a premium in an implantable devices, and because it is always desirable to make such implantable devices smaller to minimize inconvenience to the patient. That being said, FSK communications still could be used between IPG 110 and an external controller in addition to the optical communications disclosed herein. As an additional benefit, optical communications will not be subject to or provide electromagnetic interference. This can simplify circuit design in the disclosed IPG and external controllers, as coupling between such circuitry and the coils 34 or 54 is a non-issue.

Optical communications between the IPG 110 and the external charger may also render certain aspects of the prior art IPG 10 and external charger 70 unnecessary. For example, because the external charger and IPG 110 can communicate optically via link 101b, LSK communications from the IPG 110 to the external charger may not be necessary, and hence relevant LSK circuitry in both devices are shown in dotted lines (FIG. 14A). That being said, LSK communications still could be used between IPG 110 and an external charger in addition to the optical communications disclosed herein.

Optical communications also allows for the integration of the external controller and the external charger in a single device. For example, FIG. 17 shows an integrated external controller/charger 300 in the form of a modified external controller 150 (see FIG. 9). In external device 300, coil 54 (previously used for FSK telemetry) has been replaced by a charging coil 302 used to provide the magnetic charging field 80 to charge the IPG's battery. To assist with alignment determinations, the window assembly 304 and underlying photoemitter 164 and photodetector 166 have been moved to be generally centered with respect to the coil 302. In this example, the external controller/charger 300 is integrated in a unitary housing, i.e., case 59.

The external device 300 can operate in an IPG communications mode having functionality similar to the external charger to set or adjust the therapy settings the IPG 110 provides to the patient, and to receive relevant data from the IPG 110. The external device 300 can also operate in a charging mode to produce the magnetic charging field. These modes can operate and use optical communications to beneficial ends as discussed previously. Note that redundancies in the external controller and the external charger can be eliminated in the integrated external device 300. For example, the external device 300 may have only one optical transmitter (e.g., 144; FIG. 10) coupled to photoemitter 164, and one optical receiver (e.g., 146, FIG. 10) coupled to one photodetector 166, which would handle optical communications for all modes of operation. External device 300 may also have additional photodetectors to allow for alignment direction determinations (FIGS. 15A-15D), and may position the optical devices differently with respect to the case 59 (FIG. 9).

FIG. 18 shows a modified external device 300' having integrated communication and charging capability, which uses a combined communication/charging head 350. Like the heads 210 and 250 described earlier (FIGS. 11 and 16), the head 350 is coupled by a cable 352 to a mobile controller. The head 350 is essentially similar to the charging head 250 described earlier and can be modified as explained earlier (additional photodetectors, different placement of the optical devices, etc.), although optical communications related to external controller functionality are also passed between the head 350 and the IPG 110 in addition to optical communications used for charging. Otherwise, the external device 300' can operate as external device 300, providing both communication and charging functionality, with the additional convenience of separating the graphical user interface from aspects of the system that need to be proximate to the IPG 110.

Other modifications to the disclosed devices and techniques are possible. For example, the optical radiation used in optical communications need not have a fixed wavelength, but can comprise radiation with a wider frequency spectrum. Optical communications used in different directions (e.g., link 101a, 101b), can occur at different wavelengths, which may facilitate full duplex communications on these links More than one set of photoemitters and corresponding photodetectors may be used to respectively transmit and receive optical radiation in a given direction along a communication link, which may operate at different wavelengths. The circuitry disclosed herein can also be modified in any number of ways. For example, instead of programming modules in the various control circuitries of the devices, such modules can exists as discrete circuits outside of their control circuitries.

While it is preferred to use a single window assembly 112 in the IPG 110, number of window assemblies 112 can be used as well. For example, although not depicted, the IPG 110 could contain two window assemblies 112 on its top side, one of which contains a photoemitter 114 and the other which contains a photodetector 116. The external controller or charger could likewise contain two window assemblies, one of which contains a photoemitter and the other which contains a photodetector. This would allow different optical links to be supported in different directions (101a and 101b) through different sets of windows. Providing different numbers of window assemblies 112 on the IPG 110, or a larger window assembly containing a number of photoemitters or photodetectors, may also be useful in determining and indicating alignment. For example, the alignment procedure described above can essentially be reversed, with the external charger providing pulses from its photoemitter, which intensity is detected at a number of photodetectors in the IPG, with such intensities optically reported to the external charger for alignment interpretation. Different window assemblies 112 operating at different wavelengths that correspond with different window assemblies in the external charger can also be used for alignment.

Another window assembly placed elsewhere on the IPG, for example on its bottom side facing inwardly of the patient, may also be useful to allow the IPG 110 to optically communicate with other implanted devices, such as another IPG 110.

Use of the window assembly 112 on the side of the IPG 110's case 12 is preferred, but not necessary in all manners in which optical communications are useful. For example, if optical communications are used to provide visual feedback regarding IPG operations, conditions, or codes to a manufacturer, clinician, or patient as described earlier, positioning of the photoemitter 114 that provides such indications is less critical. If used for such purposes, the photoemitter 114 could be placed elsewhere, such as in the header 28 (FIG. 1A), and electrically coupled to the circuitry inside the case via additional feedthrough wires between the case 12 and the header 28. Or the photoemitter 114 could be placed inside the case, with radiation optically ported through the feedthrough, using a lens, a fiber optical cable, a window, or other structure. A special optical feedthrough different from that used for the electrodes wires could also be provided. Suitable visual indications can be provided even if the optical radiation in these scenarios will travel through more complicated or optically bulky structures.

Visual indications are especially useful to display operations, conditions, or codes before implantation, such as during manufacturing, or surgery. Particularly useful is optically providing a visual indication of a "go/no-go" signal to the implanting clinician before the IPG is implanted in the patient. In this regard, the IPG 110 can be configured to detect the impedance at each electrode 16 after the electrode lead(s) 18 are connected to the IPG 110. If any electrode is not within a proper impedance range (e.g., if an electrode is measured to have an open or short circuit), a "no-go" signal could be visually indicated by a photoemitter placed anywhere on the IPG. The implanting clinician can then attempt to re-secure the leads until a "go" signal is visually indicated, at which point the clinician could then safely implant the IPG. Alternatively, the "no-go" signal might indicate a particular electrode that is not being measured with a suitable impedance.

Providing optical communication functionality to the external devices (e.g., the external controller and external charger) may also be beneficial as an easier way to communicate with or test such devices, or to allow them to optical communicate with each other or with other external devices.

The following claims at times recite "a" structure, but this should not be construed as limiting scope to devices that only contain a singular one of such structures.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger for an implantable medical device, comprising:
    a charging coil configured to provide a charging field to charge a battery in the implantable medical device during a charging session; and
    at least one photodetector configured to receive at least one optical signal from the implantable medical device, wherein the external charger is configured to determine an alignment between the external charger and the implantable medical device by comparing an intensity of the at least one optical signal to a threshold, wherein the threshold is determined after implantation of the implantable medical device in a patient.

2. The external charger of claim 1, wherein at least one photodetector is centered with respect to the charging coil.

3. The external charger of claim 1, further comprising a case, and wherein the at least one photodetector is provided through one or more holes in the case.

4. The external charger of claim 1, further comprising a case, and wherein the at least one photodetector is located on an outside of the case.

5. The external charger of claim 1, further comprising a case and a window affixed to the case, wherein the at least one photodetector is configured to optically receive the optical signal through the window.

6. The external charger of claim 5, wherein the window comprises a lens.

7. The external charger of claim 1, further comprising receiver circuitry coupled to the at least one photodetector configured to demodulate the at least one optical signal into a series of digital data bits.

8. The external charger of claim 7, wherein the at least one optical signal comprises one or more of a voltage of the battery, a charging current of the battery, and a temperature measured by the implantable medical device.

9. The external charger of claim 7, wherein the at least one optical signal comprises an instruction for the external charger to begin generating the charging field.

10. The external charger of claim 7, wherein the at least one optical signal is received by the external charger during production of the charging field.

11. The external charger of claim 10, wherein the at least one optical signal comprises data used to control the charging field.

12. The external charger of claim 11, wherein the external charger is configured to control the charging field by controlling an energy or a duty cycle of the charging field.

13. The external charger of claim 1, wherein the external charger is further configured to determine a direction that the external charger can be moved to improve alignment between the external charger and the implantable medical device by assessing the at least one optical signal.

14. The external charger of claim 13, wherein the external charger comprises a plurality of photodetectors arranged radially with respect to the charging coil, and wherein the external charger is configured to determine the direction by assessing the received intensity of the at least one optical signal at the plurality of photodetectors.

15. The external charger of claim 1, wherein the external charger comprises a mobile controller and a charging head, wherein the charging coil and the at least one photodetector are located in or on the charging head.

16. The external charger of claim 1, further comprising a photoemitter configured to transmit an optical signal to the implantable medical device.

17. The external charger of claim 1, wherein the at least one optical signal is received prior to the charging session.

18. The external charger of claim 17, wherein the at least one optical signal causes the external device to start generating the charging field.

19. The external charger of claim 1, wherein the external charger is configured to provide an indication of misalignment when the intensity of the at least one optical signal is less than the threshold.

20. The external charger of claim 19, further comprising a speaker, wherein the indication of misalignment is provided via the speaker.

* * * * *